(12) United States Patent
Hennink et al.

(10) Patent No.: US 6,395,302 B1
(45) Date of Patent: May 28, 2002

(54) METHOD FOR THE PREPARATION OF MICROSPHERES WHICH CONTAIN COLLOIDAL SYSTEMS

(75) Inventors: Wilhelmus Everhardus Hennink, Waddinxveen; Okke Franssen, Utrecht, both of (NL)

(73) Assignee: Octoplus B.V. (NL)

( * ) Notice: Subject to any disclaimer, the term of this patent is extended or adjusted under 35 U.S.C. 154(b) by 0 days.

(21) Appl. No.: 09/503,847

(22) Filed: Feb. 15, 2000

Related U.S. Application Data

(63) Continuation-in-part of application No. 09/308,349, filed on May 19, 1999.

(30) Foreign Application Priority Data

Nov. 19, 1996 (EP) .............................................. 96203234

(51) Int. Cl.[7] .............................. A61K 9/14; A61K 9/16; A61K 9/00; B01J 13/02; A01N 25/26
(52) U.S. Cl. ........................ 424/489; 424/400; 424/417; 424/490; 424/497; 264/4.1; 264/4.3; 427/213.36
(58) Field of Search ................................. 424/490, 489, 424/400, 497, 417; 264/4.3, 4.1; 427/213, 36

(56) References Cited

U.S. PATENT DOCUMENTS

| | | | | |
|---|---|---|---|---|
| 4,921,757 A | * | 5/1990 | Wheatley et al. | ......... 428/402.2 |
| 4,963,367 A | | 10/1990 | Ecanow | ....................... 424/485 |
| 5,639,441 A | * | 6/1997 | Sievers et al. | ................ 424/9.3 |
| 5,674,521 A | | 10/1997 | Gehrke et al. | ............... 424/423 |

FOREIGN PATENT DOCUMENTS

EP  0 213 303 A2  *  6/1986

OTHER PUBLICATIONS

De Smedt et al. "Characterization of the Network Structure of Dextran Glycidyl Methacrylate Hydrogels by Studying the Rheological and Swelling Behavior", Macromolecules 28, (1995) 5082–5088.
Gehre et al. "Enhanced Loading and Activity Retention of Proteins in Hydrogel Delivery Systems", Proceed. Intern. Symp. Control. Rel. Bioact. Mater., 22 (1995) 145–146.
Heller et al. "Controlled Release of Water–Soluble Macromolecules from Bioerodible Hydrogels", Biomaterials 4 (1983) 262–266.
Hennink et al. "Controlled Release of Proteins from Dextran Hydrogels", Journal of Controlled Release 39 (1996), 47–57.
Kim et al. "Hydrogels: Swelling, Drug Loading and Release", Pharmaceutical Research 9(3) (1992) 283–290.
M. Bradford, "A Rapid and Sensitive Method for the Quantitation of Microgram Quantities of Protein Utilizing the Principle of Protein–Dye Binding", Anal. Biochem. 72 (1976) 248–254.
Van Dijk–Wolthuis et al. "Synthesis Characterization and Polymerization of Glycidyl Methacrylate Derivatized Dextran", Macromolecules 28, (1995), 6317–6322.

* cited by examiner

*Primary Examiner*—Thurman K. Page
*Assistant Examiner*—S. Tran
(74) *Attorney, Agent, or Firm*—Morrison & Foerster LLP

(57) ABSTRACT

The invention relates to a method for the preparation of microencapsulated colloidal systems such as liposomes, i.e., microspheres which comprise colloidal systems. These microencapsulated colloidal systems can be used as controlled release systems for the delivery of active ingredients in in vivo and in vitro applications. A method is provided in which the colloidal systems are added to a phase which comprises a water soluble crosslinkable polymer followed by formation of microspheres.

29 Claims, 18 Drawing Sheets

Volume particle size distribution of dextran microspheres

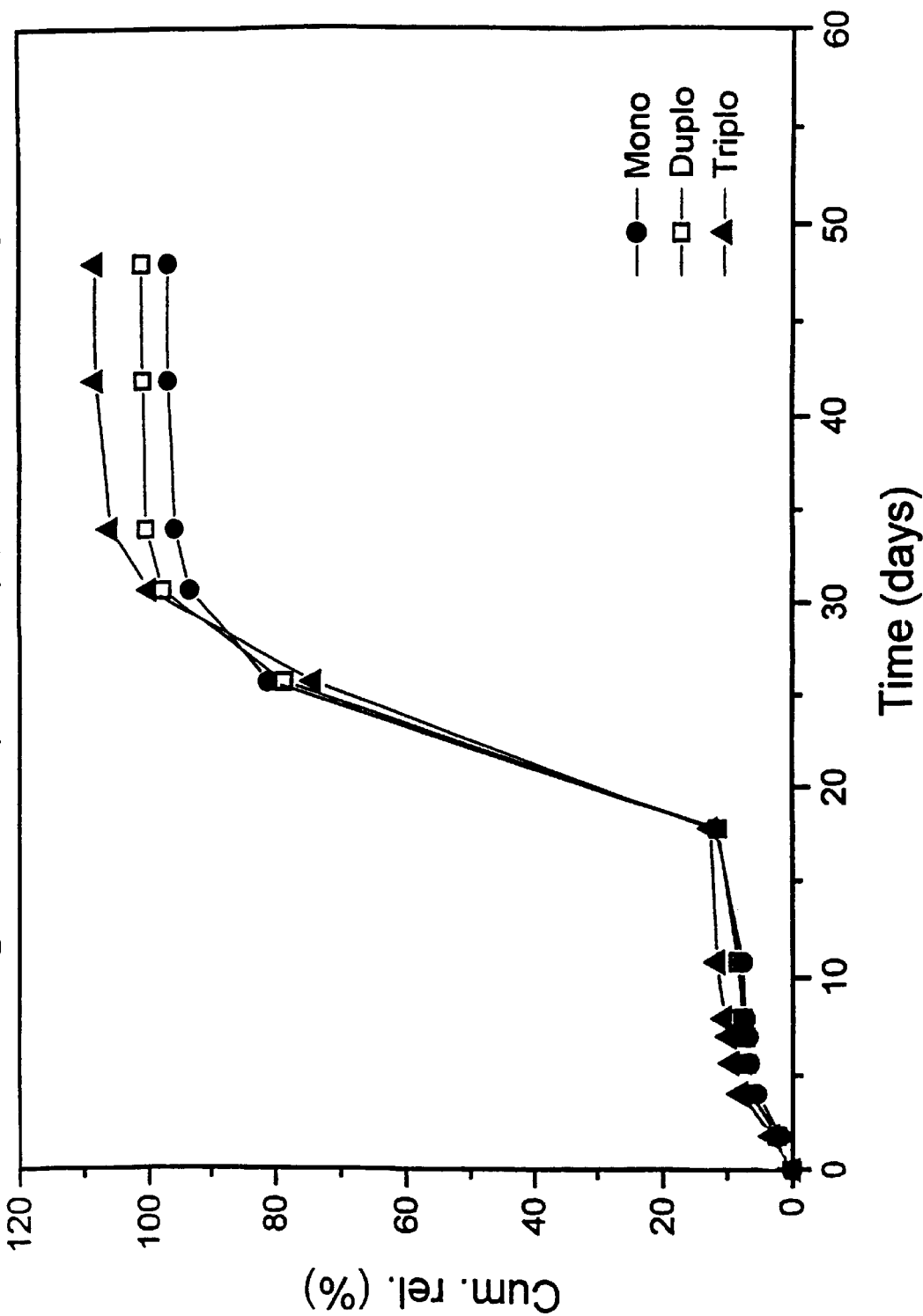
Figure 9 Reproducibility, pH 7.2 (99082501.org)

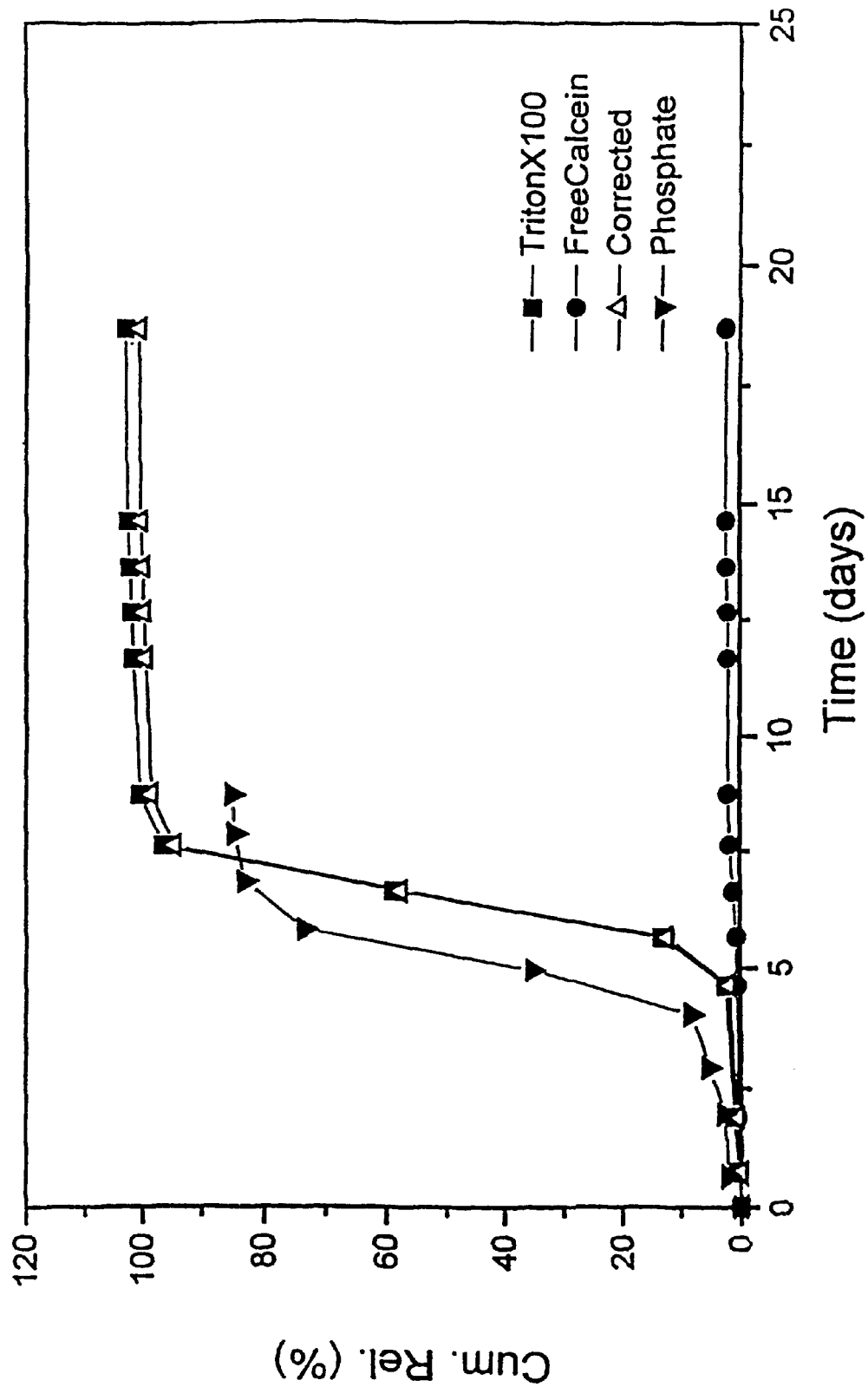
Figure 10 Release of free, total and liposomal calcein and phosphate, pH 8.0 (99082510.org)

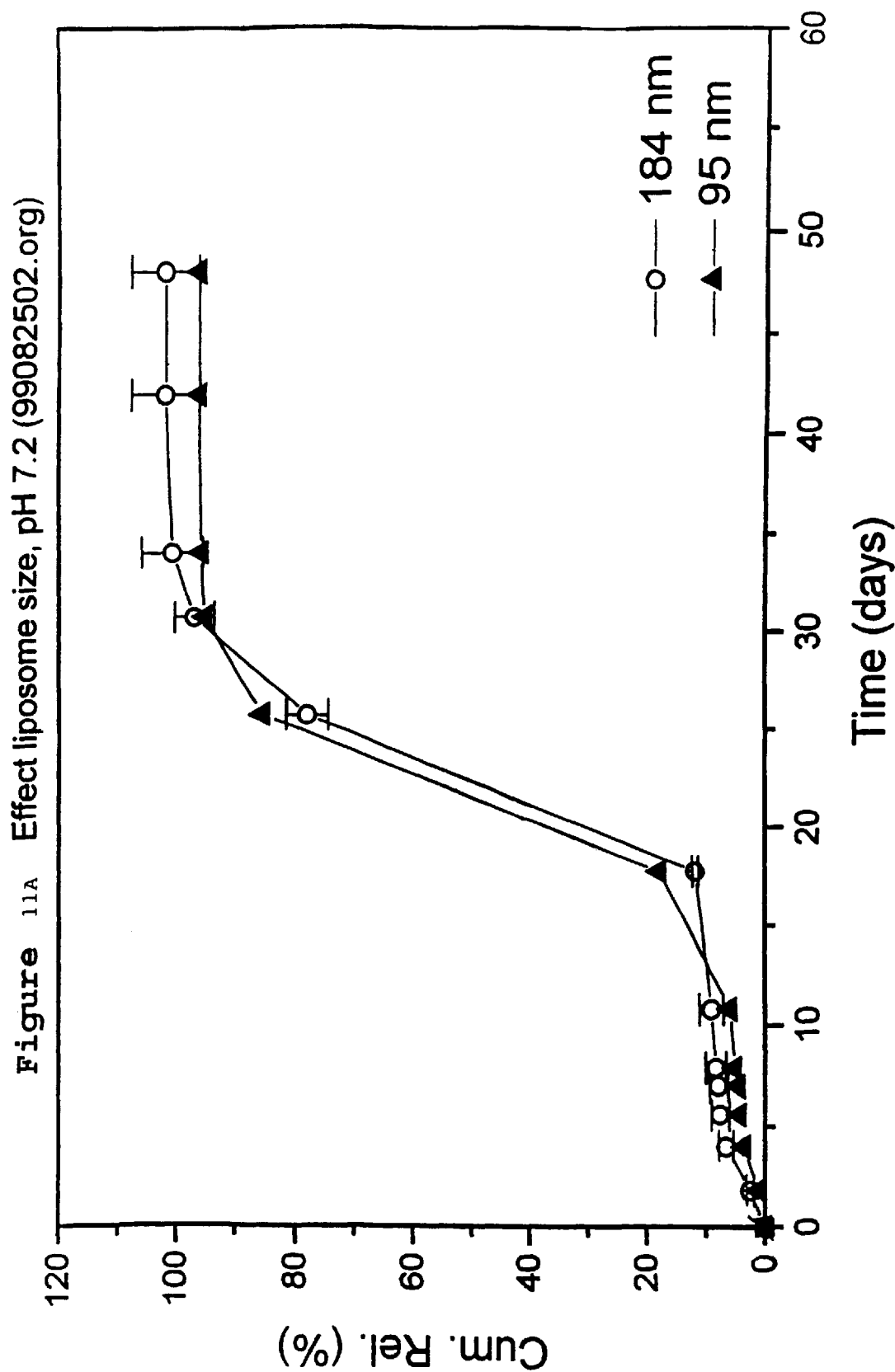
Figure 11A  Effect liposome size, pH 7.2 (99082502.org)

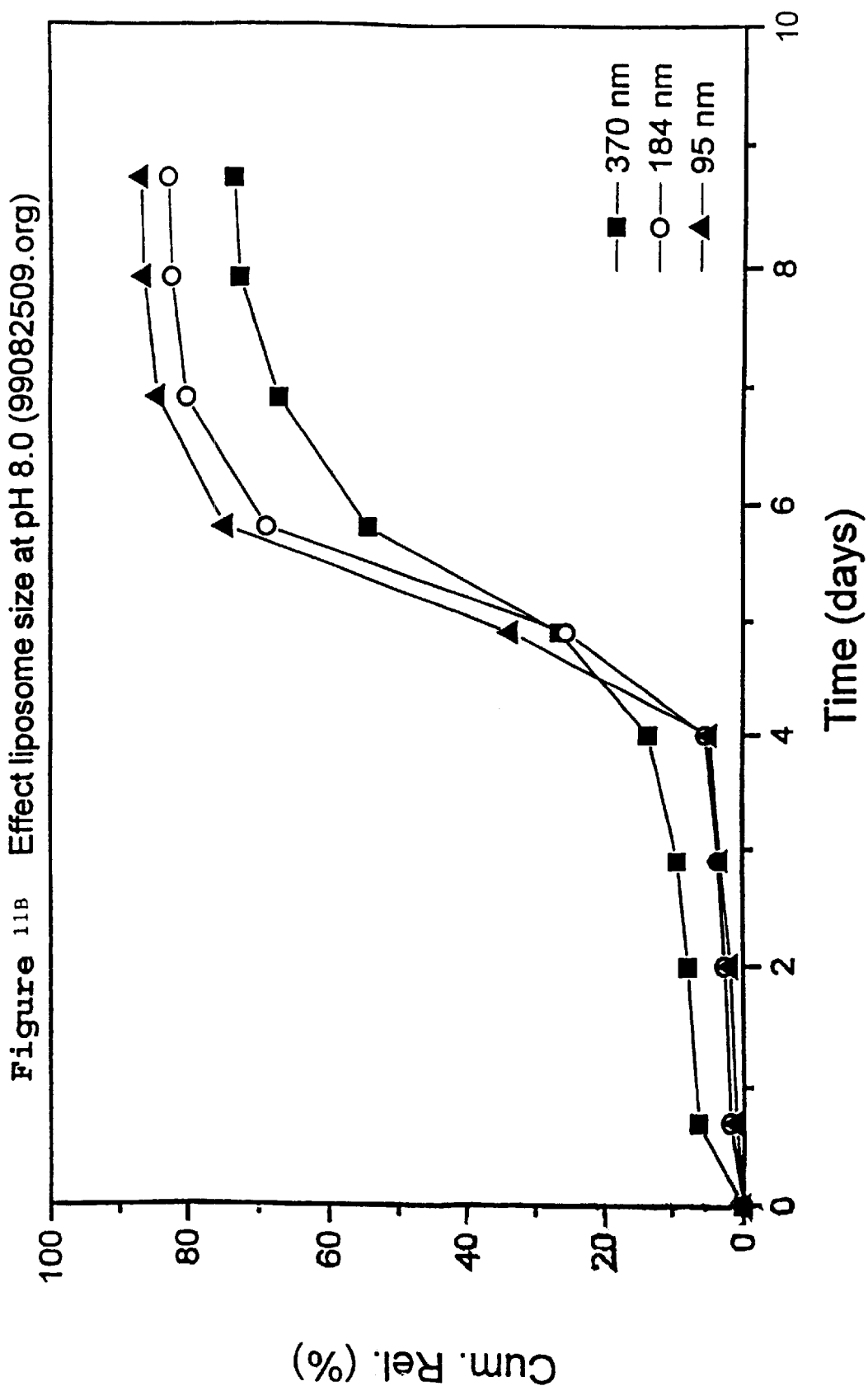
Figure 11B  Effect liposome size at pH 8.0 (99082509.org)

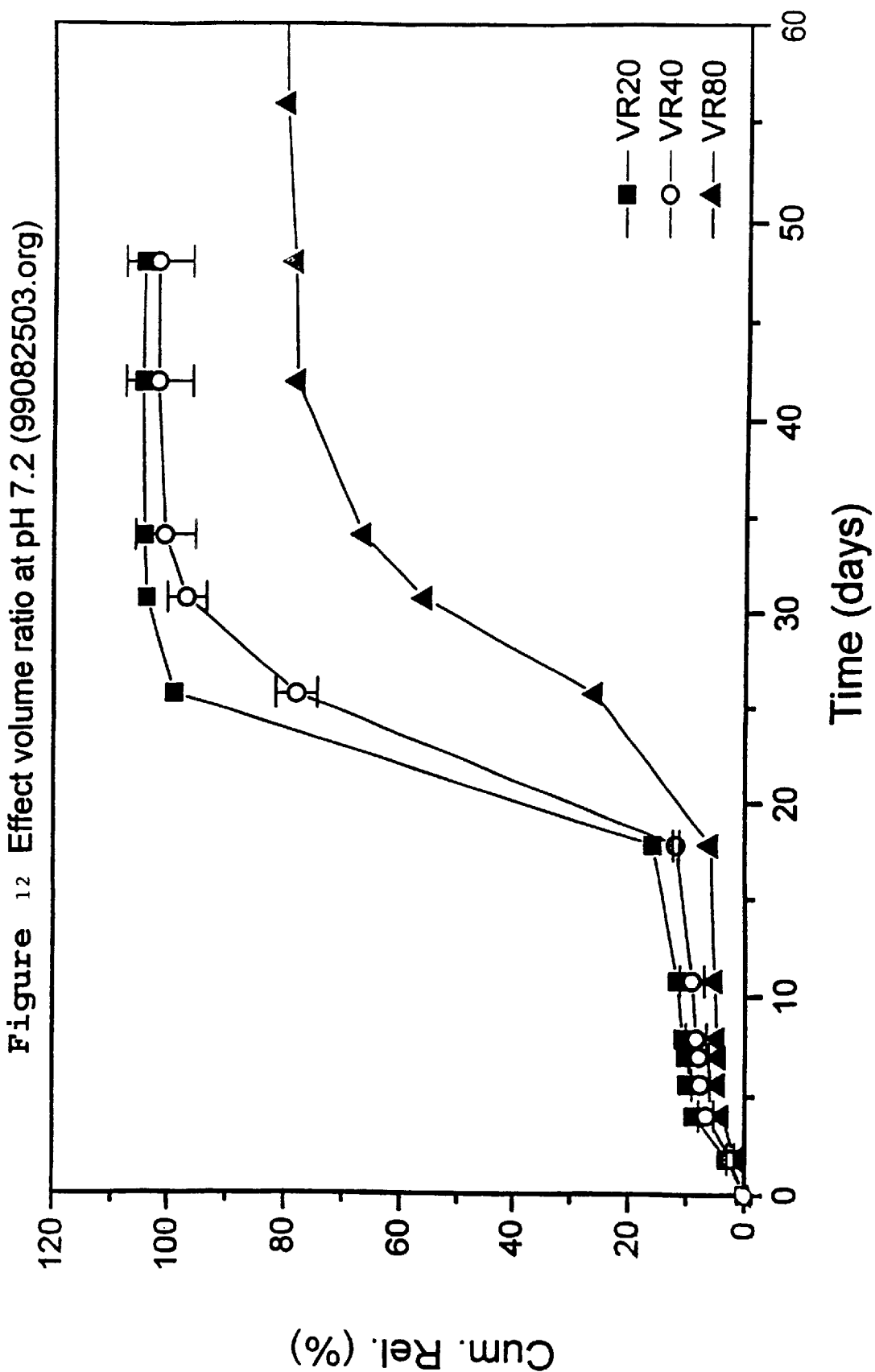
Figure 12 Effect volume ratio at pH 7.2 (99082503.org)

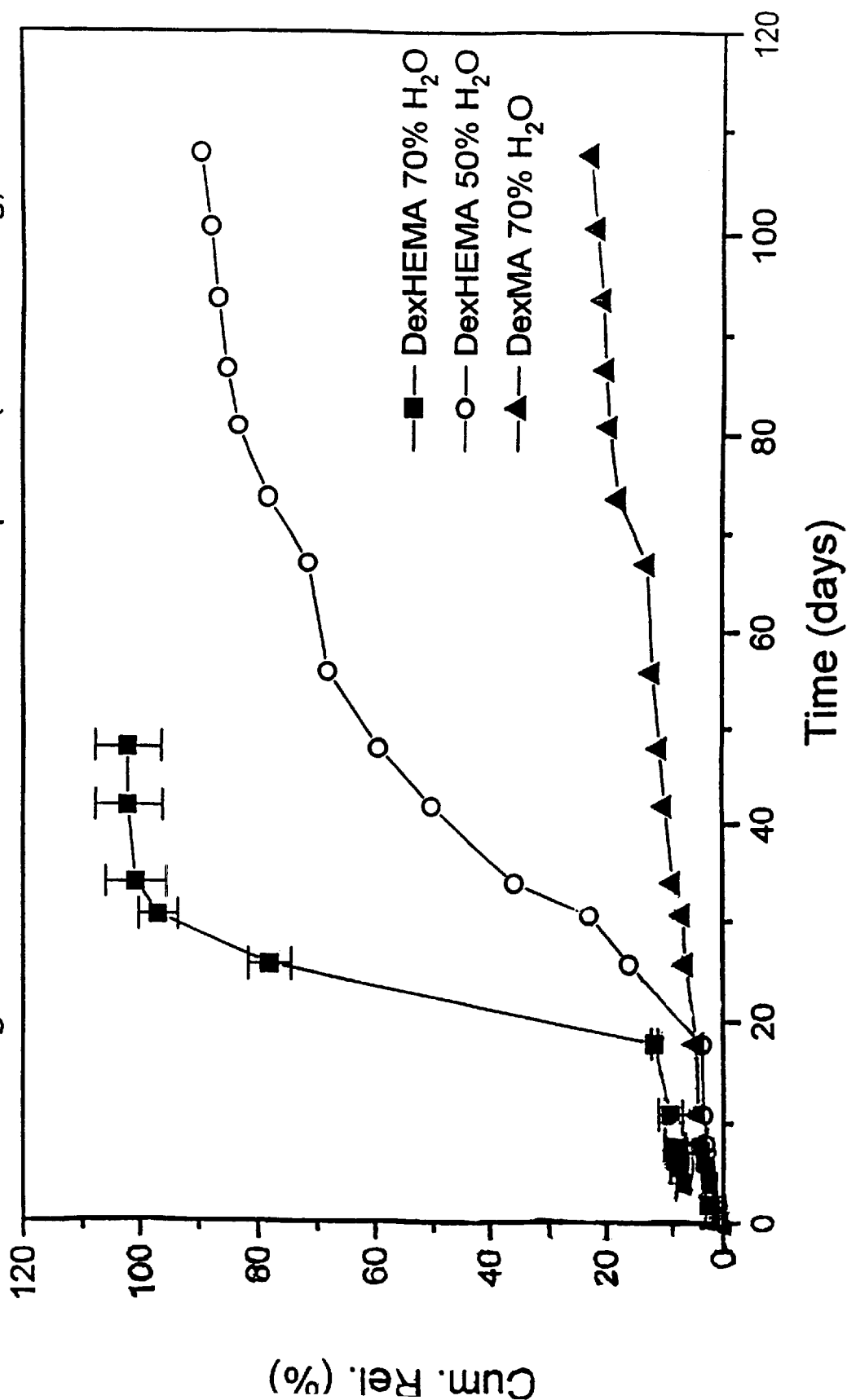
Figure 13A Effect water content at pH 7.2 (99082504.org)

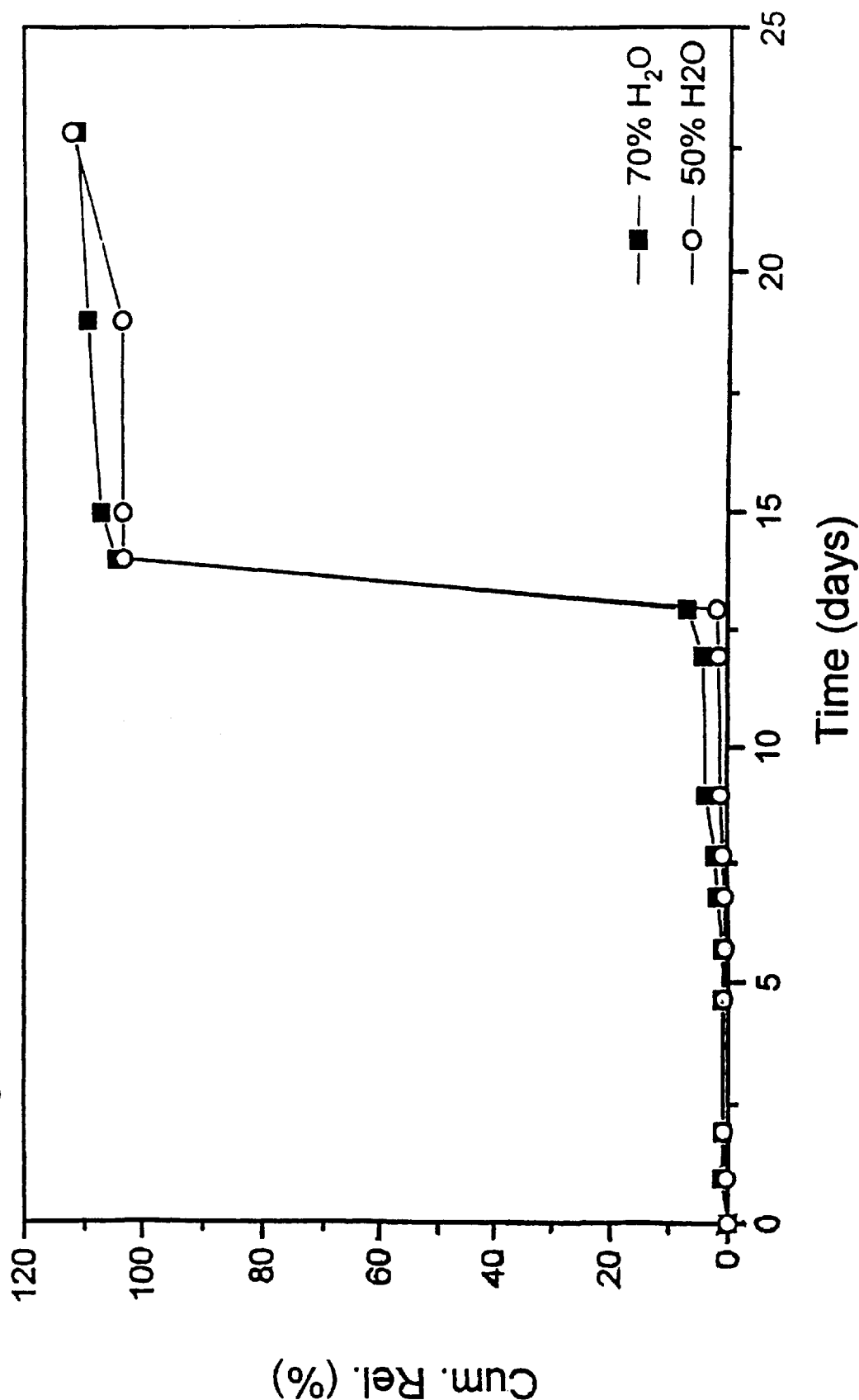
Figure 13B  Effect of water content for DS 5, pH 7.2 (99082508.org)

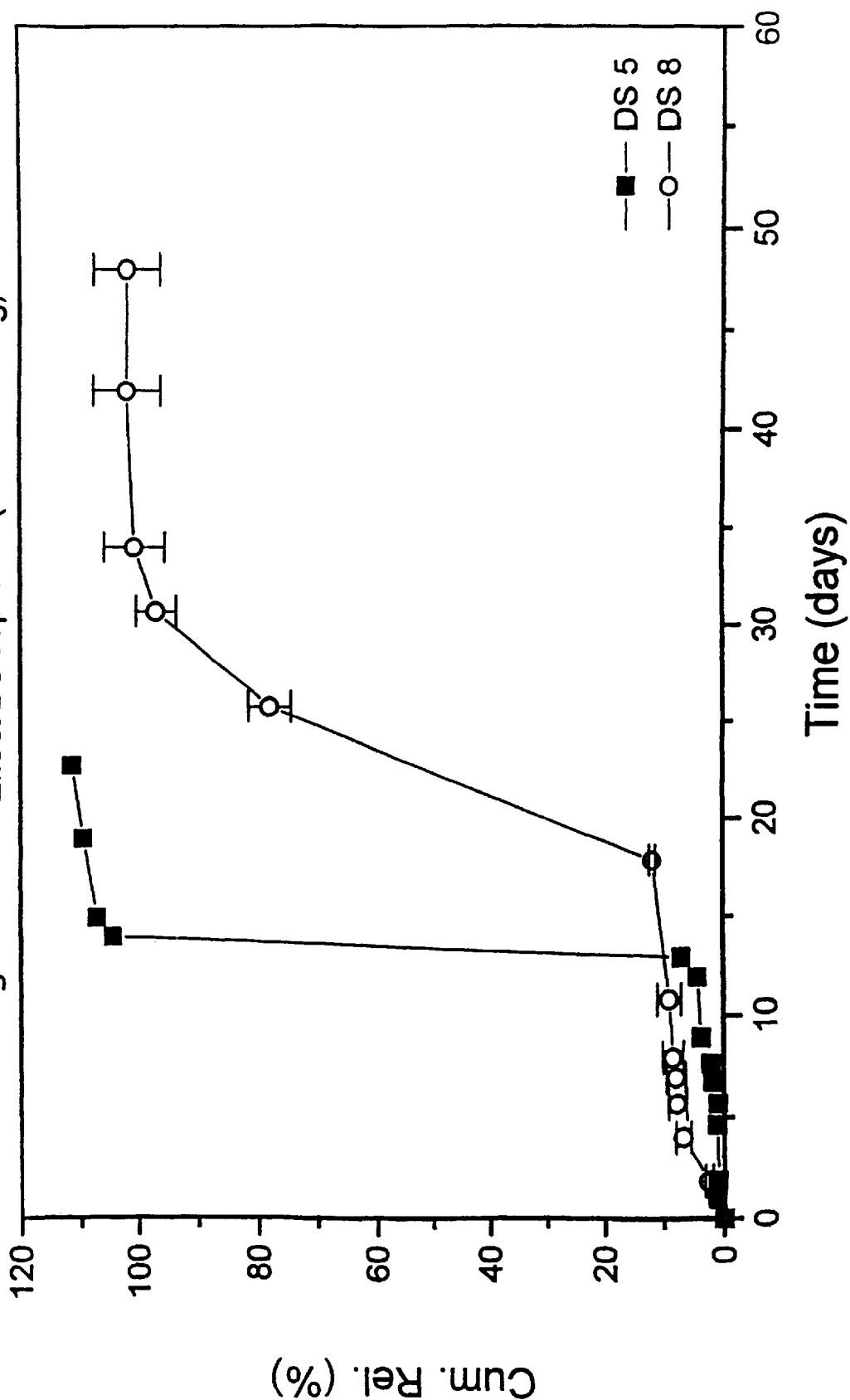
Figure 14A  Effect DS at pH 7.2 (99082506.org)

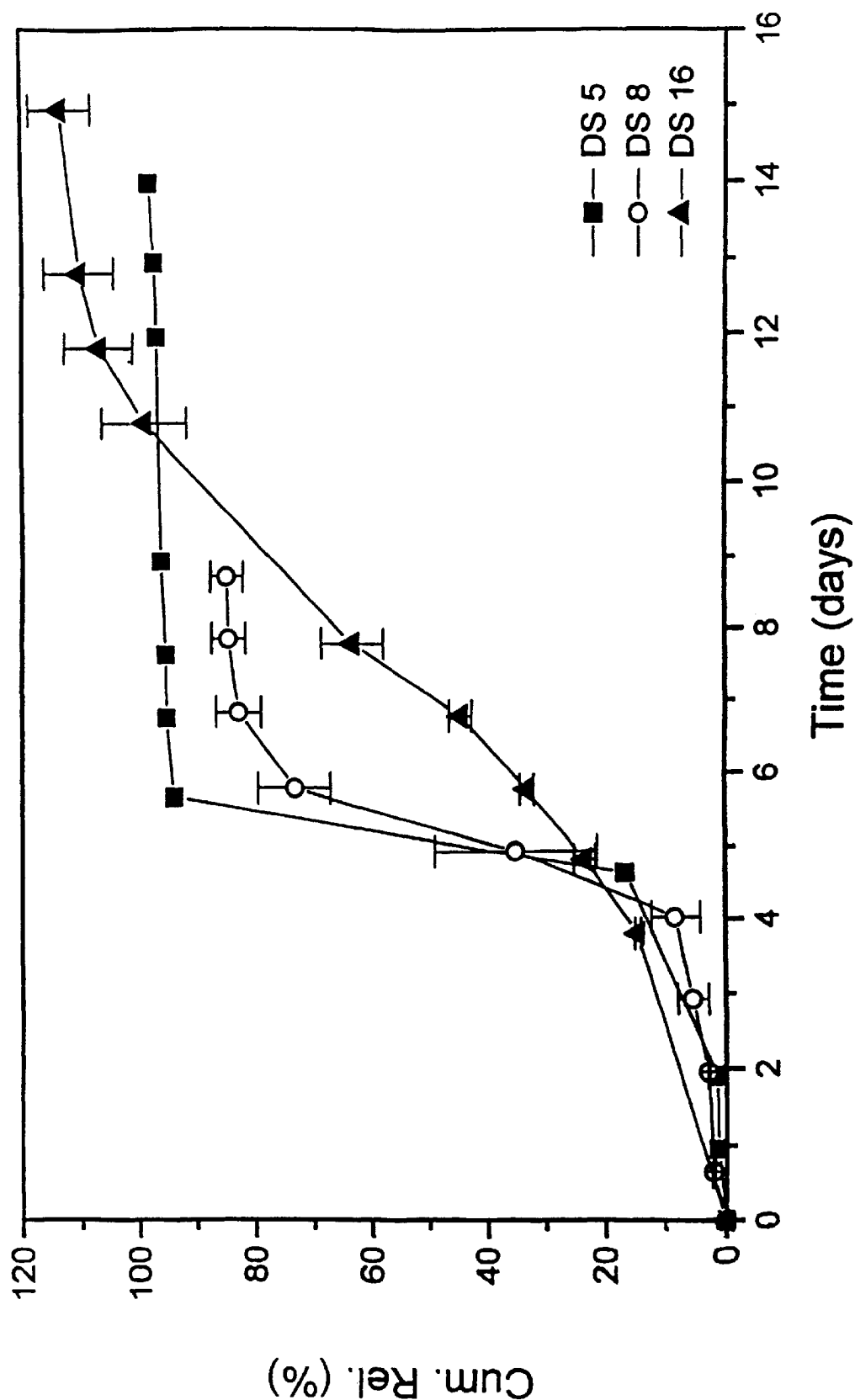
Figure 14B  Effect of DS at pH 8.0 (99082505.org)

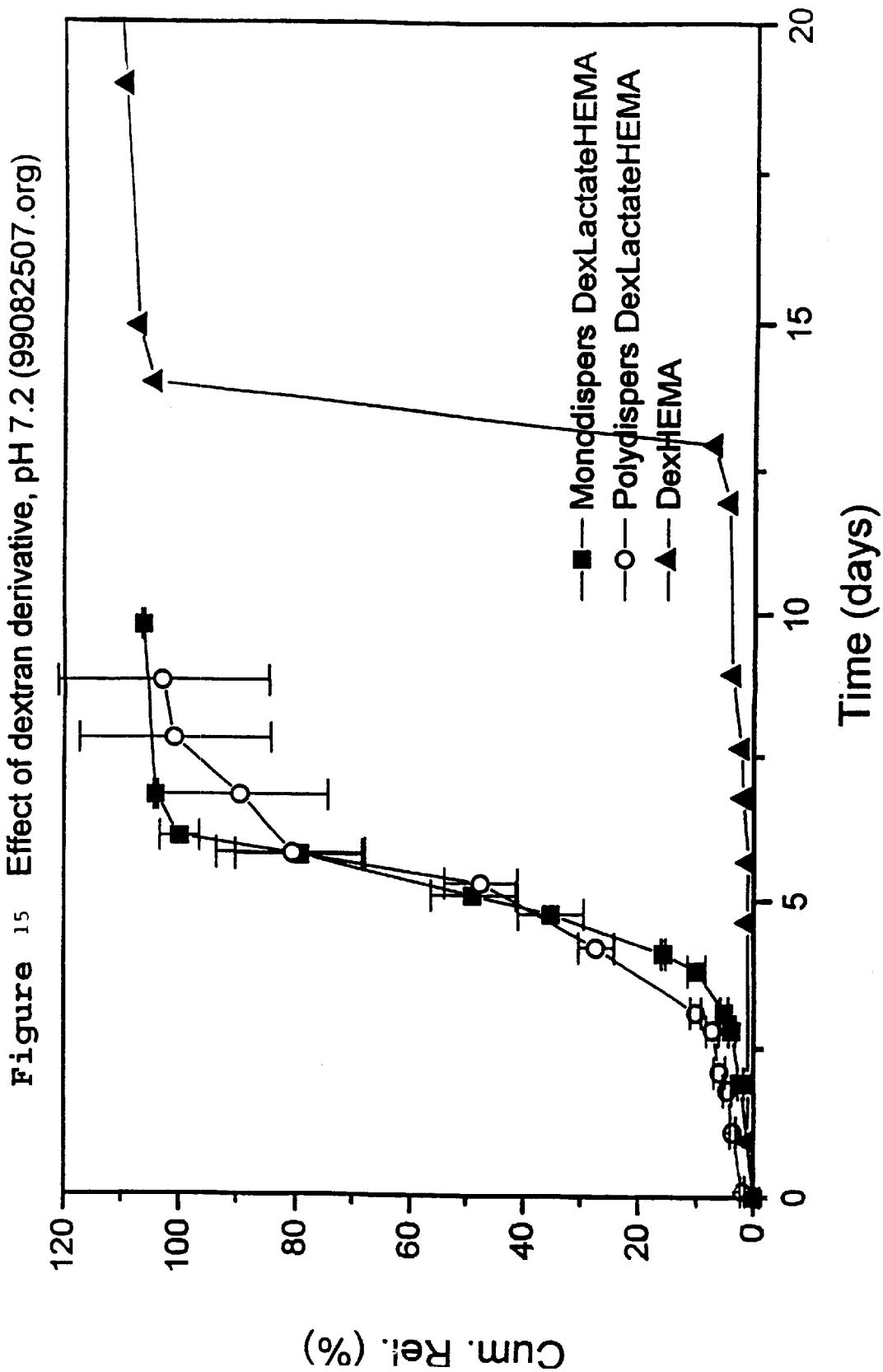
Figure 15 Effect of dextran derivative, pH 7.2 (99082507.org)

METHOD FOR THE PREPARATION OF MICROSPHERES WHICH CONTAIN COLLOIDAL SYSTEMS

This is a continuation-in-part of U.S. patent application Ser. No. 09/308,349, filed on May 19, 1999.

FIELD OF THE INVENTION

The present invention relates to a process for the preparation of a system having good controlled release behavior, and to microspheres with a good controlled release behavior. More in particular the invention relates to a method for the preparation of microencapsulated colloidal systems, i.e., microspheres which comprise colloidal systems, such as liposomes. These microencapsulated colloidal systems can be used as controlled release systems for the delivery of active ingredients in in vivo and in vitro applications.

BACKGROUND OF THE INVENTION

The fast developments in the biotechnological field lead to a large number of pharmaceutically interesting products, esp. proteins, peptides and genes. Such products can suitably be used in the treatment of life-threatening diseases, e.g. cancer, and several types of viral, bacterial and parasitic diseases.

Due to their nature, proteins and proteinaceous products, e.g. peptides, which group of products will be referred to as protein drugs herein-below, cannot efficiently be administered orally. They have to be brought in the system parenterally, i.e. by injection. The pharmacokinetic profile of these products is such that injection of the product per se requires a frequent administration. In other words, since protein drugs are chemically and physically unstable in the gastro intestinal tract and generally have a short active residence time in the human or animal body, multiple injections in a short time are required to attain a therapeutic effect. It will be evident that this is inconvenient for patients requiring these protein drugs.

For this reason, there is a need for delivery systems which have the capacity for sustained release. A number of options for such systems have been proposed in the art, such as the use of synthetic biodegradable, rather well-defined polymers to control the release of encapsulated drugs.

One of the options described in the prior art is the use of microspheres and nanospheres made of polymeric materials. These microspheres or nanospheres are spherical particles, spherical capsules, nanocapsules or nanoparticles having a particle diameter between about 0.1 $\mu$m and about 100 $\mu$m. In this description and the claims, the reference to microspheres also encompasses microparticles, microcapsules, nanospheres, nanoparticles and nanocapsules. Widely used polymers to prepare these microspheres are poly lactic acid and copolymers of lactic acid and glycolic acid. The polymers should preferably be biodegradable to avoid removal of the polymer carrier after use.

The hitherto known preparation methods for drug containing controlled or sustained release systems generally involve the use of organic solvents. Organic solvents may lead to structural changes in protein structure, esp. in the secondary and tertiary structure. Such changes may lead to a denaturation of the protein drug. Since these structural changes normally lead to a loss in pharmacological activity and the occurrence of undesired side-effects, such changes are undesirable, as will be apparent. Moreover, the use of organic solvents is not desirable from an environmental point of view, either.

Further, it is hardly possible to avoid that traces of organic solvents will remain in or on the microspheres produced. Especially, when toxic solvents are used, such as the widely applied solvents chloroform and dichloromethane, this is a problem.

Another problem is that it is difficult to encapsulate proteins in polymeric matrices in a reproducible way. It is of the utmost importance that predictable and reproducible amounts of proteins or other encapsulated products to be used as drugs are released.

Polymeric hydrogels, i.e., polymeric networks that contain a considerable amount of water, are also widely studied as controlled release systems. Although polymeric hydrogels can be applied successfully as controlled release systems, there remains a need to further modify the release profiles obtained. In particular the lag time, i.e., the time after which the onset of release occurs, and the duration of the pulse in case of pulsed release are parameters that determine the success of the application of a controlled release system to a large extent.

One of the hydrogel systems that has been used in the preparation of delivery systems for protein drugs comprises crosslinked dextrans obtained by radical polymerization of methacrylate derivatized dextran (dex-MA). In this respect, reference is made to van Dijk-Wolthuis et al. in Macromolecules 28, (1995), 6317–6322 and to Van Dijk-Wolthuis et al. in Macromolecules 30, (1997), 3411–3413.

It appeared that the release of proteins from these hydrogels depends on and can be controlled by the degree of crosslinking and the initial water content of the gel (Hennink et al., J. of. Contr. Rel. 39 (1996), 47–57, the contents thereof being incorporated herein by reference).

Encompassed drugs are released from these hydrogels or polymeric microspheres during biodegradation of the polymeric material and/or by diffusion.

Drugs are usually loaded into hydrogels or microspheres derived hereof either by equilibration in a drug-containing solution followed by drying (see e.g. Kim et al. in Pharm. Res. 9(3) (1992) 283–290) or by incorporation of the drug during the preparation of the hydrogel or microspheres (see e.g. Heller et al. in Biomaterials 4 (1983) 262–266). Both techniques have a number of disadvantages other than those arising from any organic solvents used.

Loading by equilibration normally leads to a rather low drug content in the delivery system due to entropic exclusion: larger molecules enter the hydrogel with more difficulty than smaller ones. This is especially the case, when the drug is a macromolecular compound. Unless the pore size of the hydrogel or the microsphere is rather large, the macromolecules will only adsorb onto the outer surface, which may, after application, lead to a burst release in the human or animal system or in vitro. Further, the solvent phase containing the drug, which phase is contacted with the delivery system to load the delivery system, has to be removed from the hydrogel or the microspheres. This can produce the migration of the drug to the surface of the delivery system, and, hence, to a non-homogeneous drug distribution. This tends to result in a significant burst release of the drug, as well, which generally is not desired.

A suitable loading process for incorporating macromolecular drugs is aimed at.

In an article in Proceed. Intern. Symp. Control. Rel. Bioact. Mater., 22 (1995), 145–146, Gehrke et al. have described a technique wherein loading levels higher than obtainable by solution sorption, hence, higher than about 0.1 wt. %, can be achieved in purified, pre-formed hydrogels.

The loading technique is based on the fact that certain polymer mixtures split into separate phases when dissolved in water. Proteins dissolved in such a system distribute unevenly between the phases. This principle also holds when one of the polymer phases is a crosslinked gel.

In particular, Gehrke et al. describe a crosslinked dextran gel/poly(ethylene glycol) system, and a crosslinked hydroxypropylcellulose gel/poly(vinyl alcohol) system. Proteins present in an aqueous solution containing beads of the gel are, after the addition of the non-crosslinked second polymer, adsorbed on the beads and partly absorbed through meshes or pores in the bead surfaces.

A disadvantage of this technique is that the proteinaceous material is to a major extent only adsorbed to the beads, which means that if the phase containing the second polymer is replaced by another aqueous system a fast removal of the proteins from the beads is observed. Only when large amounts of pores having a diameter larger than the size of the proteinaceous material to be loaded are present in the bead surfaces, some absorption may occur. This adsorption and limited absorption behavior has an undesirable effect on the release of the proteinaceous material from the beads.

To additionally illustrate the undesired release behavior, it is noted that the profiles shown in the article are—from a pharmacological point of view—entirely unsuitable to be used in controlled release systems.

In EP-A-0 213 303 a method for producing spherical polymer particles from systems containing two liquid aqueous phases is described. One of the two phases is dispersed in the form of droplets in the other phase to form an emulsion. Subsequently, the droplets are caused to solidify. In the phase to be dispersed, a macromolecular substance may be dissolved. Further, low molecular substances such as medicaments, vaccines and insecticides can be chemically bonded to the particle forming substance in the dispersed phase. Nothing is being said about the release behavior of the dissolved substance, nor over the application of the spherical polymer particles formed or the size thereof.

The principle of affinity partitioning in PEG-containing two-phase systems is also known from Göte Johansson, Affinity Partitioning in PEG-containing Two-phase Systems In: Topics in Applied Chemistry; Poly(ethylene glycol) chemistry, Biotechnological and Biomedical Applications, Ed. J. M. Harris, Plenum Press (1992). In this article, a two-phase system is described, which is created when an aqueous solution of dextran and polyethylene glycol (PEG) are mixed. A PEG enriched and a dextran enriched phase are formed. Proteins are partitioned unequally in such systems. These known systems are used in the purification of proteins.

Liposomes have been under investigation as controlled release systems for many years. Liposomes consist of concentric closed membranes, such as a bilayer formed by water-insoluble polar lipids, such as phospholipids. Other substances, such as cholesterol, may also be included in the membrane. These liposomes may vary in diameter from a few tens of nanometers up to micrometers. Both polar and non-polar drugs or enzymes can be encapsulated as active ingredient within liposomes. Proteins can be encapsulated in liposomes very well. When using liposomes as controlled release systems, initial high concentrations of proteins in the blood may be prevented. Such high concentrations are often undesirable, because they may lead to adverse effects in the patient and to degradation of the protein. The release of the active ingredient from the liposome may be triggered by the destabilization of the bilayer.

(Micro)encapsulation of liposomes has been reported in several instances. For example, Kibat et al. (FASEB J., 4 (1990) 2533–2539) describe microcapsules composed of a hydrogel matrix of calcium alginate. These microcapsules contain liposomes. Pulsatile release of compounds from the liposomes is obtained by coating the liposomes with phospholipase $A_2$ enzyme.

Cohen et al. (Proc. Natl. Acad. Sci. USA, 88 (1991) 10440–10444) and Cohen et al. (Proceed. Intern. Symp. Control. Rel. Bioact. Mater. 16 (1989) 71–72) also describe alginate-microencapsulated liposomes. These microencapsulated liposomes are characterized by a release profile which starts immediately, i.e., show no lag time. In addition, the release is gradual rather than pulsed.

U.S. Pat. No. 4,921,757 discloses liposomes that are encapsulated in a solid permeable plate of e.g. agarose or polyacrylamide, or in microparticles based on crosslinked alginate with a polykationogenic skin.

Yeung et al. (J. Microencapsulation, 5 (1988) 331–337) describe liposomes incorporated in nylon based microcapsules, which are prepared using a interfacial polycondensation process. The release profiles of these microencapsulated liposomes shows no lag-time. Moreover, the use of nylon makes in vivo application unlikely.

Bochot et al. (International Journal of Pharmaceutics, 162 (1998) 119–127) describe an ocular delivery system based on liposomes dispersed in a thermosensitive polyoxyethylene-polyoxypropylene copolymer gel. The system is prepared by adding liposomes to the gel.

Weiner et al. (Journal of Pharmaceutical Sciences, 74 (1985) 922–925) describe the use of a collagen gel for encapsulating liposomes. After the liposomes have been added to the collagen, gel formation is initiated by changing the temperature or the pH.

Alamelu et al. (Carbohydrate Polymers, 24 (1994) 215–221) describe a delivery system based on sequestered liposomes coupled to a chitosan gel. Gel formation is effected by addition of an alkaline solution.

Finally, DiTizio et al. (Biomaterials, 19 (1998) 1877–1884) describe a liposomal hydrogel. The gel is formed by changing the pH.

All of these prior art microencapsulated liposomes rely on enzymes to effect the release of compounds from the liposomes or do not show desirable release characteristics. In addition, the encapsulation efficiency of the prior art methods is usually too low.

The present invention is aimed at providing a new injectable, patient friendly delivery system for active ingredients, such as protein drugs or other drugs, which system is safe and biodegradable, and which system possesses well controllable delivery kinetics. The period wherein drug delivery should be guaranteed depends on the active ingredient used that preferably is protein drug, and varies between a number of days up to more than one year. In addition, high degrees of loading in the delivery system should be obtained. Moreover, the system of the present invention should be produced without needing the use of organic solvents.

It is another objective of the present invention to provide a method for the preparation of microencapsulated colloidal systems, such as liposomes, which colloidal systems may be associated with an active ingredient, which microencapsulated colloidal systems display a desirable release profile, i.e., a high release of active ingredient (preferably more than 85%), a pulsed release profile having a suitable lag-time, while these release profiles can be controlled by the method of preparation. The desirable release profile should also hold for the active ingredient which may be associated with the colloidal systems. The definition of a suitable lag-time depends on the type of application. When vaccines are used as an active ingredient, a suitable lag-time is between two weeks to one year, preferably 1–3 months.

It is another objective of the present invention to provide such a method which enables a high encapsulation efficiency of the colloidal systems, i.e., an encapsulation efficiency of more than 80%, preferably more than 90%.

SUMMARY OF THE INVENTION

The present invention is directed to a combination of colloidal systems and hydrogels used for controlled release of active ingredients.

Suitable colloidal systems which may be used in the present invention are liposomes; iscoms; polyplexes, i.e. combinations of (cationic) polymers and DNA; lipoplexes, i.e. combinations of (cationic) lipids and DNA; nanoparticles, i.e. polymer based spheres in the nanometer size range; solid lipid particles in the colloidal size range (see for example R. H. Muller et al., Pharm. Research 14 (1997) 458–462); emulsions, such as intralipid-like systems; any other entity in the colloidal size range having a low water solubility; and combinations thereof.

The combinations of colloidal systems and hydrogels according to the present invention will be illustrated hereinafter using liposomes as the colloidal system. It is to be understood that were liposomes are mentioned hereinafter, these liposomes can be replaced by any of the suitable colloidal systems mentioned above, without departing from the spirit of the invention.

The problems mentioned above are solved by a specific preparation method of controlled release systems, such as microspheres, wherein water is used as the solvent. The use of water as sole solvent system is advantageous from an environmental point of view, because of toxicological considerations and, especially, because of reasons of protein stability.

In a first aspect, the present invention provides a method for the preparation of a controlled release system, comprising:

(a) forming an aqueous two-phase system from two water soluble polymers and water and at least one releasable entity, such as a liposome or another colloidal system, the two water soluble polymers being incompatible in solution, at least one of these polymers being crosslinkable, the crosslinkable polymer phase being emulsified in the other polymer phase; and the at least one releasable entity being soluble or dispersible in the crosslinkable polymer phase in the aqueous solution;

(b) allowing the releasable entity to distribute in the crosslinkable polymer phase; and (c) crosslinking of the crosslinkable polymer.

In a preferred embodiment, the crosslinking is carried out to such a degree that the pores (meshes) in the crosslinked structure eventually formed are substantially smaller than the size of the releasable entity.

By emulsifying an aqueous crosslinkable polymer in a continuous phase comprised of water and a polymer which is not compatible with the crosslinkable polymer, and crosslinking the discontinuous phase, particles are formed. The particle size of the crosslinked polymer particles can be adjusted by changing the viscosity of one or both phases, for example by choosing polymers of different molecular weight, or by changing the volume ratio of both phases (see e.g. Stenekes et al., Pharm. Res. 15 (1998) pp. 557–561, the contents of this document being incorporated herein by reference). In this way a narrow particle size distribution can be obtained, as is described herein-below in more detail.

In a further aspect, the present invention is directed to microspheres, at least 80 wt. % thereof having a particle size of between 100 nanometer and 100 $\mu$m, which microspheres are comprised of a degradable, crosslinked polymer encapsulating at least one releasable entity, such as a liposome, the pore size of the crosslinked polymer being equal or preferably smaller than the size of the releasable entity. These microspheres are obtainable by using the process of the invention, and are free from organic solvents. Dependent on the application of the microspheres, the size can e.g. be adjusted between 1 and 50 $\mu$m, preferably between 2 $\mu$m and 25 $\mu$m, such as between 5 and 15 $\mu$m.

When the pore sizes or meshes of the crosslinked polymer are equal or smaller than the hydrodynamic diameter size of the releasable component, the releasable component is essentially released when the polymer is degraded. More in particular, in this embodiment, the crosslinked structure must be degradable in the human or animal body, so that the encapsulated releasable entity can leave the crosslinked matrix. If on the other hand, the pore sizes or meshes of the crosslinked polymer are larger than the size of the releasable component, the releasable component is at least partially released by diffusion. The pore size of the crosslinked product obtained by the process of the present invention in this way provides a perfect tool to control the release. Further, the efficiency of the incorporation of a releasable entity in such a polymer structure is very high, while the degree of loading can be adjusted up to the saturation concentration of the entity to be released.

The degradability of the crosslinked structure can be regulated in a number of ways. As a first example, it is noted that bonds can be incorporated, which are hydrolysable under physiological conditions. In this respect, reference can be made to the European patent application 96201821.4 and WO-A-98/00170, the contents of which documents are incorporated herein by reference. These patent applications teach hydrogels comprising hydrolytically labile spacers between different polymer chains. The hydrolytically labile spacers described therein can be suitably used in the present invention and the above mentioned patent applications are incorporated herein by reference.

Another example to control the degradability is the coencapsulation of an enzyme or chemical substance capable of breaking bonds in the crosslinked polymer. In a preferred embodiment of the process of the present invention the crosslinkable polymer is a dextran polymer. In this embodiment a dextranase can be added to the aqueous two-phase system before the crosslinking step or added afterwards.

The dextran polymer can suitably be used in the process of the present invention together with Pluronic® or a polyethylene glycol, which latter polymer is preferred to be used in the process of the present invention.

The product aimed at by the process of the present invention can be separated from the other polymer phase using conventional techniques, for instance centrifugation and decantation.

In a first step of the process of the present invention an aqueous two-phase system is formed. This two-phase system comprises water, and at least two water soluble polymers, which polymers are incompatible in solution. Preferably an entity to be released is also present, although it is possible to add the entity to be released after the crosslinking step. The colloidal systems used in the present invention are however generally too large to enter the microspheres after the crosslinking step in a sufficient amount, in particular when liposomes are used as the colloidal system. Therefore it is preferred to add these colloidal systems before the crosslinking step. At least one of the polymers present in the aqueous phase is chemically or physically crosslinkable, and the crosslinkable polymer phase is emulsified in the other aqueous polymer phase.

The polymers used can be chosen dependent on the nature of the entity to be released. It is preferred that the entity to be released will have a clear preference for the crosslinkable polymer phase. In that case, the highest possible degree of loading, theoretically up to the saturation concentration, in the microspheres to be made, can be obtained.

It is not critical which crosslinkable polymer is used. However, if the controlled release system comprising the polymer in crosslinked form is intended to be brought into a human or animal body, the polymer should be pharmaceutically acceptable and preferably should be degradable. Suitable crosslinkable water soluble polymers are dextrans and derivatized dextrans, starches and starch derivatives, cellulose derivatives such as hydroxyethyl and hydroxypropyl cellulose, polyvinylpyrrolidone, proteins and derivatized proteins, and so on. The molecular weight of the crosslinkable polymers used normally lies between 1,000 and 1,000,000 Da. It is noted that with a higher molecular weight of the polymer, a better phase separation is generally obtained in the aqueous solution used in the process of the invention.

The person skilled in the art will have the knowledge to choose the crosslinkable polymer and the crosslinking conditions required for the emulsion prepared. For instance, dextrans can be crosslinked with methylacrylate or methacrylate groups. Another example is a system comprising PVP as the external phase and dextran as the emulsified phase, wherein the dextran is crosslinked through the presence of isocyanates.

Further, reference is made to crosslinking using radiation. Dex-MA (methacrylate derivatized dextran) can e.g. be polymerized using small dosages of γ-radiation, such as less than 0.1 Mrad. An advantage of this embodiment is that in one step sterile microparticles can be obtained. Further, crosslinking by UV radiation and physical crosslinking using e.g. hydrophobic tails coupled to a polymer are possible techniques.

In a preferred embodiment, the crosslinkable polymer is a temperature sensitive polymer such as poly-N-isopropylacrylamide, which polymer can, e.g., be present as a graft on another polymer such as a dextran. Hydrogels of these polymers show increasing swelling behavior at degreasing temperatures. This makes it possible that releasable material can easily penetrate in the hydrogel after the crosslinking reaction. By subsequently raising the temperature, e.g. to a value of 37° C., the meshes in the hydrogel shrink, thereby capturing the releasable entity.

The polymer which is present in the aqueous continuous phase can be any polymer which is incompatible with the crosslinkable polymer. Although this polymer may also be crosslinkable, but of course not under the reaction conditions used for the crosslinking of the discontinuous polymer phase, this is not preferred. Examples of suitable polymers incompatible with the polymer to be crosslinked are poly (ethylene glycol) (PEG) and poly(vinyl alcohol) (PVA) (in combination with e.g. dextrans and dextran derivatives, starches and starch derivatives, PVP, and water soluble cellulose derivatives).

The release of the releasable entity depends on a number of variables, which can be used to tailor the delivery as desired. One of these variables is the size of the microspheres. The size can be adjusted by carefully modifying the process circumstances and formulation parameters in the emulsifying step. For instance, the water content, the presence of hydrophobic groups on any one of the polymers or mixtures of polymers used, the viscosity of the continuous and discontinuous phase, and the electrical charge on the at least two polymers used are examples of tools to adjust the size of the microspheres or microparticles to be produced. In addition, emulsifiers can be added. Suitable emulsifiers are copolymers, preferably block-copolymers, of units of the two incompatible polymers, e.g. a block-copolymer of PEG and dextran, used to create the two-phase system.

To further guarantee a controlled release, the crosslinked polymer should preferably be degradable.

As said herein-above, it is important that the two water soluble polymers are incompatible with one another, so that a two-phase system is obtained after the two polymers have been added to each other in an aqueous solution. Whether or not a two-phase system will be obtained depends not only on the nature of the two polymers involved, but also on the conditions under which they are added. Factors that are relevant in this regard are the molecular weight of the polymers, their concentrations in the aqueous solution, the temperature at which they are added to one another, and so forth. It is part of the standard skills of the artisan to determine a phase diagram for any combination of polymers that can be used, and thus to choose suitable conditions for obtaining a phase separation.

In the attached FIG. 8 a phase diagram of a water/PEG/dextran ternary system is shown as example. When the starting-composition is below the binodal (- - -), a one phase system is present, whereas above the binodal, two coexisting phases are formed: one enriched in polymer 1 (composition $x_1$) and the other enriched in polymer 2 (composition $x_2$)—$x_1$ and $x_2$ are connected via a tie-line (__). All systems prepared using starting-compositions on the same tie-line separate into phases of constant composition. For a given starting-composition, the volume ratio of the coexisting phases $x_1/x_2$ equals $y_2/y_1$.

As indicated herein-above, the releasable entity can be a protein drug. However, it is also possible to encapsulate a pharmacon or antigen or other active agents containing colloidal systems, such as nanoparticles or microparticles, e.g. liposomes and iscoms. The encapsulation of this type of particles has the advantage of preventing the occurrence of a too fast release of the encapsulated entity, or, said in other words, burst-effects can be avoided in a more secure way.

The microencapsulated colloidal systems obtained by the method of the invention comprise a matrix of a degradable polymer in which the colloidal systems, such as liposomes, are present. Active ingredients may be present in the colloidal systems. It is a considerable advantage of the present invention that these active ingredients may be chosen in principle regardless their compatibility with the polymeric matrix, i.e. it is not required that the active ingredients are soluble or dispersible in the matrix itself, since it is sufficient that these active ingredients are compatible with the colloidal system. This enables the preparation of release systems comprising active ingredients which could only with difficulty or only with additional measures, be incorporated in release systems of the prior art.

The method of the invention thus enables microspheres for e.g. the delayed or pulsed release of all types of active ingredients. When liposomes are used as the colloidal systems, the presence of the bimolecular lipid membrane layer enables the incorporation of hydrophobic substances, which could not be brought in conventional hydrogel systems. These hydrophobic substances can be incorporated in, or associated with the lipid bilayer.

Examples of colloidal particles to be encapsulated are: iscoms, lipoplexes, polyplexes, nanoparticles and solid liponanoparticles.

Iscoms may be released by the microspheres slowly or in a pulsed manner. This allows the designer of vaccines to manipulate the immune response induced by the antigen-carrying iscoms. E.g., if a booster is desired, the microspheres can induce a booster effect by pulsed release of the iscoms after a predetermined delay time.

It may be desired to have access to delivery systems that release polyplexes and lipoplexes (complexes of genetic material and condensing polymer (mixtures) or (mixtures) in a time controlled way. The microspheres are able to do that.

The same applies to nanoparticles and lipospheres, which can be loaded with therapeutically active material or antigens. Nanoparticles are colloidal particles based on e.g. polycyanoacrylates. Solid lipid nanoparticles are colloidal particles based on lipids which are in the solid phase at body temperature. Nanoparticles and solid lipid nanoparticles can be released from the microspheres in similar patterns as liposomes. Drug release from these colloidal particles depends on their building components and manufacturing conditions.

Moreover, by incorporating the active ingredient in the colloidal system, the active ingredient is protected from the reactions that take place during the subsequent polymerization step, which reactions could cause undesired oxidation of the active ingredient.

With the method of the invention, it is possible to provide microcapsules which comprise 10 wt. % or more of the colloidal system. Usually, the amount of incorporated colloidal system will be from about 5–10 wt. % but this amount will vary with the specific conditions used.

The amount of active ingredient which may in total be incorporated as well in the microsphere, as the efficiency of this incorporation, will also vary strongly depending on synthesis conditions and envisaged application. For example, if a membrane protein is to be incorporated in a liposome, it will be readily absorbed in the bilayer of the liposomes. These liposomes can be incorporated into microspheres with high efficiencies, as was stated above. On the other hand, a hydrophilic protein will be incorporated less efficiently in the liposome, resulting in lower protein content of the final microsphere. If microspheres with a high content of active ingredient are desired, a more hydrophilic colloidal system can be used.

Typically, the amount of active ingredient present in the microspheres prepared with the method of the present invention, will be from about 0.5–50 µg active ingredient/mg microsphere material.

The partition of the entity to be released is primarily determined by the nature of the polymers present in the aqueous two-phase system. This partition can be influenced, e.g. by adding salt to the aqueous system, or by adjusting the pH.

If the releasable entities, such as proteins, are present during the crosslinking step, care should be taken that the integrity of the releasable entities is secured. It should for instance be avoided that proteinaceous material is oxidized by initiator systems etc. In this light, it is noted that adverse effects can be avoided or minimalized by minimalizing the amount of initiator, reducing the polymerization time or adding suitable antioxidantia, such as α-tocopherol.

The separation of the crosslinked structures enclosing the releasable entity from the other phase can be carried out in any conventional way. Preferably, the separation is effected by filtration or centrifugation. The crosslinked structures can subsequently be washed with water and dried. The drying step determines that a pharmaceutically acceptable product can be obtained, having a maintenance term of more than 2 years. A very preferred drying method is spray-drying, although the drying can also be suitably carried out using lyophilization.

BRIEF DESCRIPTION OF THE DRAWINGS

FIG. 9 shows liposome release for 3 individually prepared batches of dextran microspheres at pH 7.2. The formulation of the microencapsulated liposomes being: DexHEMA DS 8, water content 70%, PEG/dex volume ratio: 40, 184 nm DPPC:DPPG:Chol (10:1:10) liposomes.

FIG. 10 shows the release of free calcein, total calcein, liposomal phosphate at pH 8.0. The formulation at the microencapsulated liposomes being: DexHEMA DS 8, water content: 70%, PEG/dex volume ratio: 40, DPPC:DP-PG:Chol (10:1:10) liposomes with (226 nm) and without (184 nm) calcein.

FIG. 11A shows the effect of liposome size on the release characteristics at pH 7.2. The formulation of the microencapsulated liposomes being: DexHEMA DS 8, water content: 70%, PEG/dex volume ratio: 40, 95 and 184 DPPC:D-PPG:Chol (10:1:10) liposomes.

FIG. 11B, shows the effect of liposome size on the release characteristics at pH 8.0. The formulation of the microencapsulated liposomes being: DexHEMA DS 8, water content: 70% PEG/dex volume ratio: 40, 95 and 184 DPPC:D-PPG:Chol (10:1:10) liposomes.

FIG. 12 shows the effect of the PEG/dex volume ratio on the release characteristics at pH 7.2. The formulation of the microencapsulated liposomes being: DexHEMA DS 8, water content: 70% PEG/dex volume ratio: 20, 40, and 80, 184 nm DPPC:DPPG:Chol (10:1:10) liposomes.

FIG. 13A shows the effect of the water content on the release characteristics of microencapsulated liposomes according to the invention at pH 7.2, compared with release from non-degradable dexMA microspheres. The formulation of the microencapsulated liposomes being: DexHEMA DS 8, water content 70 and 50%, PEG/dex volume ratio: 40, 184 nm DPPC:DPPG:Chol (10:1:10) liposomes.

FIG. 13B shows the effect of the water content on the release characteristics at pH 7.2. The formulation microencapsulated liposomes being: DexHEMA DS 5, water content: 70 and 50%, PEG/dex volume ratio: 40, 184 nm DPPC:DPPG:Chol (10:1:10) liposomes.

FIG. 14A shows the effect of the degree of substitution on the release characteristics at pH 7.2. The formulation of the microencapsulated liposomes being: DexHEMA DS 5 and 8, water content: 70%, volume ratio: 40, liposome size: 184 nm.

FIG. 14B shows the effect of the degree of substitution on the release characteristics at pH 8.0. The formulation of the microencapsulated liposomes being: DexHEMA DS 5, 8 and 16, water content: 70% volume ratio: 40, liposome size: 184 nm.

FIG. 15 shows the effect of dextran derivative on the release characteristics at pH 7.2. The formulation of the microencapsulated liposomes being: DexHEMA (DS 5), mono- and polydiperse dexLactateHEMA (DS 4), water content: 70%, volume ratio: 40, liposome size 184 nm.

DETAILED DESCRIPTION OF THE INVENTION

Figure 1:
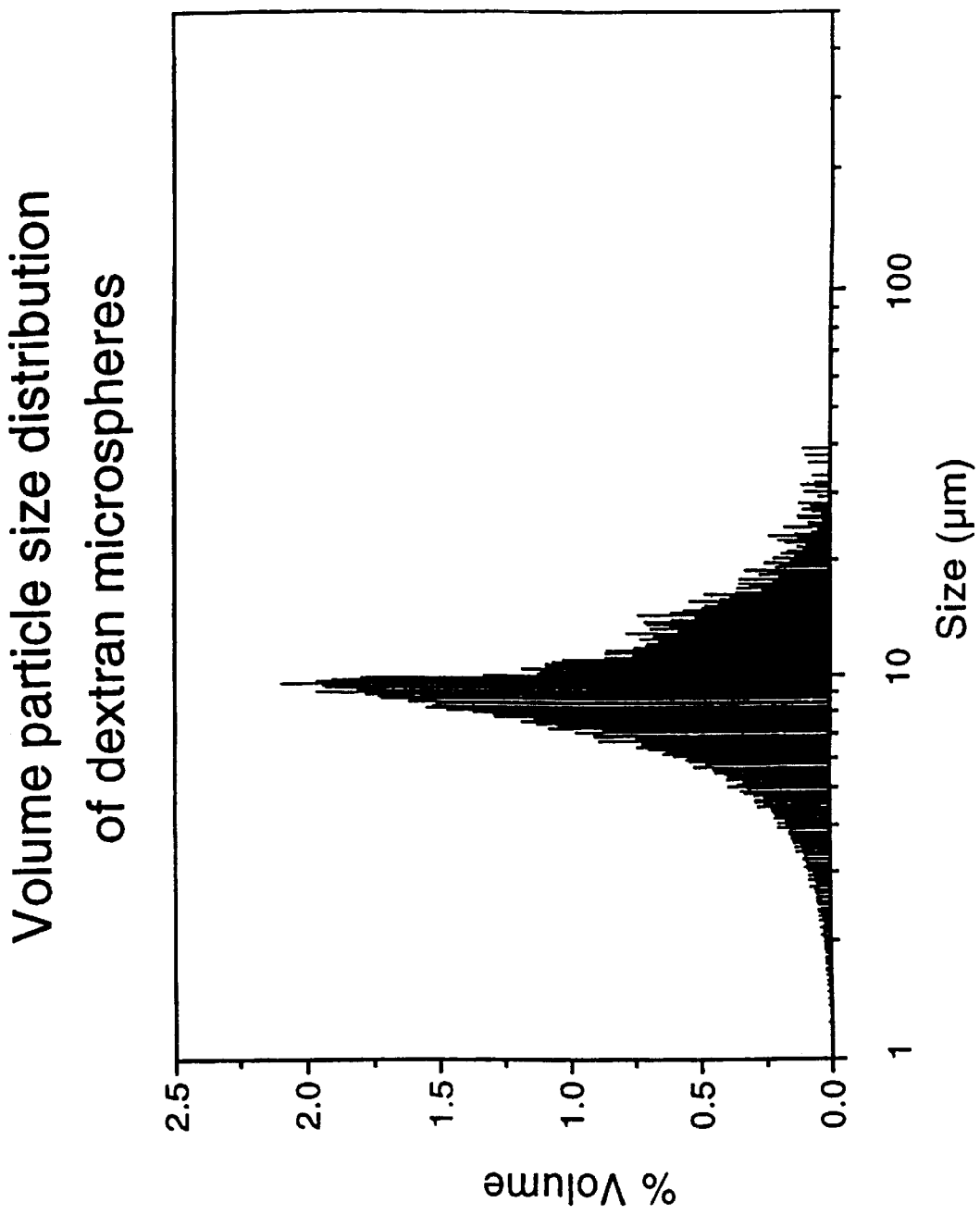
FIG. 1 shows a volume particle size distribution of dextran microspheres prepared via the water-in-water emulsion technique.

The present invention provides a method for the encapsulation of colloidal systems, such as liposomes, in crosslinked microspheres.

The present inventors surprisingly have found, that when microspheres which comprise colloidal systems are prepared according to a method which comprises the steps of:
  a) providing an aqueous mixture of i) a first phase comprising a water soluble crosslinkable polymer, ii) a second phase comprising a water soluble polymer which is incompatible in solution with the polymer in said first phase, and iii) colloidal systems to be suspended in said first phase; forming an emulsion of said first phase in said second phase, and
  b) forming microspheres in the emulsion by crosslinking at least part of said crosslinkable polymer, thus forming said microencapsulated colloidal systems, the problems mentioned herein-above can be overcome.

In a preferred embodiment, the method of the invention is carried out by first mixing the colloidal systems with said first phase and subsequently contacting this mixture with said second phase. By forming a premixture by contacting said colloidal systems with said first phase in step a), and subsequently contacting this premixture with said second phase, the colloidal systems can be encapsulated in the microspheres with very high encapsulation efficiencies.

When applying the microencapsulated colloidal systems produced according to the invention, a large part of the colloidal systems is released intact from the microspheres, yielding a desirable release profile. Over a broad size range, the release profile is not affected by the size of the colloidal systems used. Moreover, the release profile can be tailored by modifying certain steps in the method of the invention, as will be explained herein-below.

The preparation of the microencapsulated colloidal systems, such as liposomes, according to the invention is carried out using water as the continuous phase, i.e. as the solvent or the dispersifying phase. This is advantageous from a toxicological point of view. Moreover, the absence of organic solvents prevents the degradation of the colloidal systems and the active ingredient comprised by the colloidal systems.

In accordance with the present invention it has been found that colloidal systems such as liposomes can be encapsulated in microspheres and especially dextran microspheres with very high encapsulation efficiencies. With the method according to the invention, almost complete—i.e. more than 85 wt. %, preferably more than 90 wt. %—of the amount of colloidal systems added to the initial mixture can be obtained.

The colloidal systems are released intact from degradable microspheres and a pulsed release can be obtained. Also systems showing delayed release upon application can be obtained. The release period under physiological conditions can be tailored from e.g. 6 days (dexLactateHEMA DS 4, water content 70%, volume ratio: 40) to e.g. 3 months (dexHEMA DS 8, water content 50%, volume ratio: 40). Extrapolated from release experiments at pH 8.0, the release using dexHEMA DS 16 under physiological conditions using a water content of 50%, was even longer than 3 months.

A longer pulse is generally observed for microspheres with a lower water content and a higher degree of substitution due to slower degradation of the microsphere.

DexLactateHEMA microspheres generally release colloidal systems faster than dexHEMA, because the lactate ester is more susceptible to hydrolysis than the carbonate ester.

The crosslinkable polymer used should be pharmaceutically acceptable and preferably be degradable. Suitable crosslinkable water soluble polymers are dextrans and derivatized dextrans, starches and starch derivatives, cellulose derivatives such as hydroxyethyl and hydroxypropyl cellulose, polyvinylpyrrolidone, proteins and derivatized proteins. A preferred crosslinkable polymer is dextran comprising crosslinkable groups. Preferred crosslinkable groups are methacrylate groups, most preferred dextran polymers being selected from the group consisting of dexMA, dexHEMA and dexLactateHEMA.

The process of the present invention will be further illustrated herein-below by the preparation of dextran microspheres which comprise liposomes as the colloidal system, using the water-in-water emulsion technique.

EXAMPLES

The microencapsulated liposomes of the invention will now be illustrated with the following non-limiting examples, with reference to FIGS. 9–15.

Example 1

Polyethylene glycols (PEG) with varying molecular weights were obtained from Merck-Schuchardt, Germany. Methacrylate derivatized dextrans (dex-MA) with varying DS (degree of substitution; the number of methacrylate groups per 100 glucopyranose residues) were synthesized by a coupling reaction of dextran T40 and glycidyl methacrylate in DMSO (dimethylsulfoxide) using DMAP (N,N-dimethylamino-pyridine) as a catalyst, essentially as described by Van Dijk-Wolthuis et al. in Macromolecules 28, (1995) 6317–6322.

Dex-PEG was synthesized as follows. mPEG (monomethoxy-polyethylene glycol, M 5000 g/mmol, 5 g, corresponding with 1 mmol hydroxyl groups) and CDI (carbonyldiimidazole, 162 mg, 1 mmol) were dissolved in 100 ml of anhydrous tetrahydrofuran. The solution was stirred overnight at room temperature, followed by the evaporation of the solvent under reduced pressure. Next, the CI (carbonylimidazole) activated mPEG was added to a solution of dextran T40 (1.7 g) and DMAP (0.35 g) in 50 ml DMSO. This solution was stirred for one week at room temperature. After neutralization of DMAP with HCl, the solution was extensively dialyzed against water and subsequently freeze dried. The product was characterized by gel permeation chromatography and NMR. The degree of substitution amounted to 4 Dex-lactate-HEMA (DS 3) was synthesized as described in the copending European patent application No. 96201821.4.

Polyethylene glycol (PEG, varying molecular weight) was dissolved in 0.22 M KCl to a concentration of 12–40% (w/w) Dex-MA was dissolved in 0.22 M KCl to a concentration of 10–40% (w/w). Both solutions were flushed with nitrogen for 10 minutes. Next, 4.75 ml of the PEG solution and 0.25 ml of the dex-MA solution were mixed and vortexed (Winn Vortex-Genie, maximum speed) for 1 minute resulting in a water-in-water emulsion with dextran as the inner phase and PEG as the outer phase. After 10 minutes ((N,N,N',N'-tetramethyl-ethylenediamine, 100 μl, 20% (v/v) in 0.22 M KCl pH adjusted with concentrated HCl to 7.2) and KPS (potassium peroxydisulfate, 180 μl, 50 mg/ml in water) were added. The emulsion was incubated for 30 minutes at 37° C. to polymerize the dex-MA. The microspheres were washed twice with water and freeze dried.

It was demonstrated using in vitro cell cultures that cytotoxicity of dex-MA is low, similar to the cytotoxicity of dextran, which compound has been used for years as plasma replacing agent in human beings.

The particle size (number weight diameter ($=\Sigma nd/\Sigma n$) and volume weight diameter ($=\Sigma nd^4/\Sigma nd^3$), I. C. Edmundson, Particle-size analysis, H. S. Bean, A. H. Beckett and J. E. Carles (eds) in: Advances in Pharmaceutical Sciences vol.2, Academic Press, London 1967, 95–174) and particle size distribution were determined by a laser light blocking technique (Accusizer™, model 770, Particle Sizing Systems, Santa Barbara, Calif., USA). The shape and surface characteristics (porosity) of the microspheres were established by scanning electron microscopy (SEM) analysis.

Figure 2:
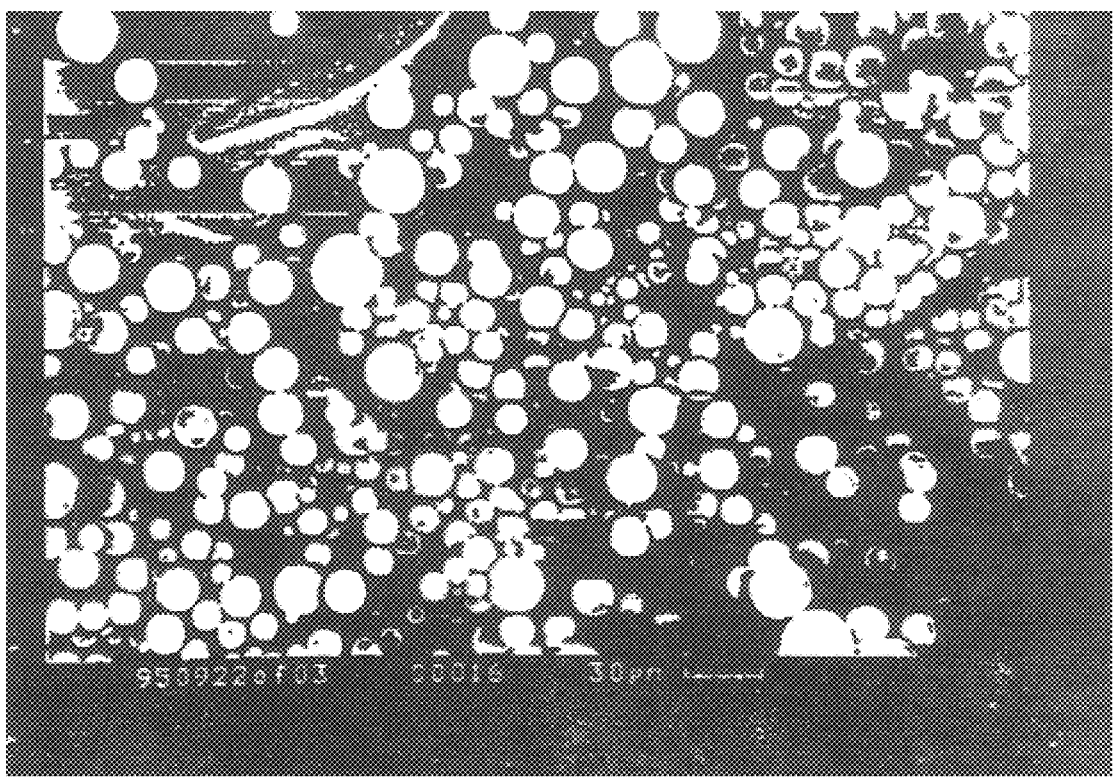
FIG. 2 shows a SEM micrograph of the dextran microspheres of FIG. 1.

FIG. 1 gives a representative example of particle size distribution of a dextran microsphere batch prepared via the water-in-water emulsion technique as determined using the Accusizer. SEM analysis showed that the particles are perfectly spherical and non-porous (FIG. 2).

Figure 3:
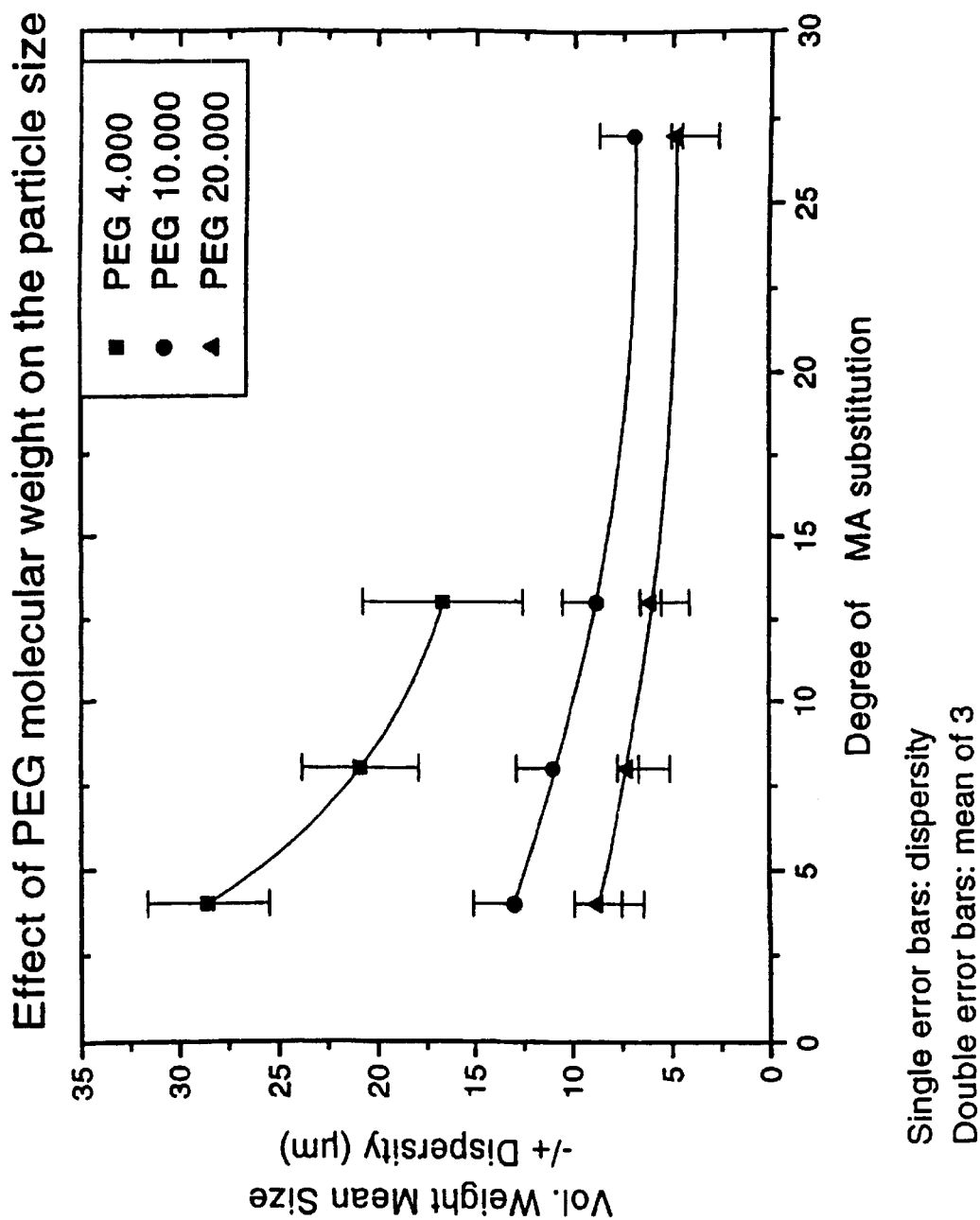
FIG. 3 shows the volume weight average diameter of dextran microspheres as a function of the degree of MA substitution and the molecular weight of PEG.

FIG. 3 shows the volume weight average diameter of dextran microspheres as a function of the degree of MA substitution and the molecular weight of PEG. The concentration of the PEG solution was 24% (w/w); the concentration of the dex-MA concentration was 20%. It is shown that the particle size increases with decreasing molecular weight of PEG. At a fixed molecular weight of PEG, the particle size slightly decreases with increasing DS.

Figure 4:
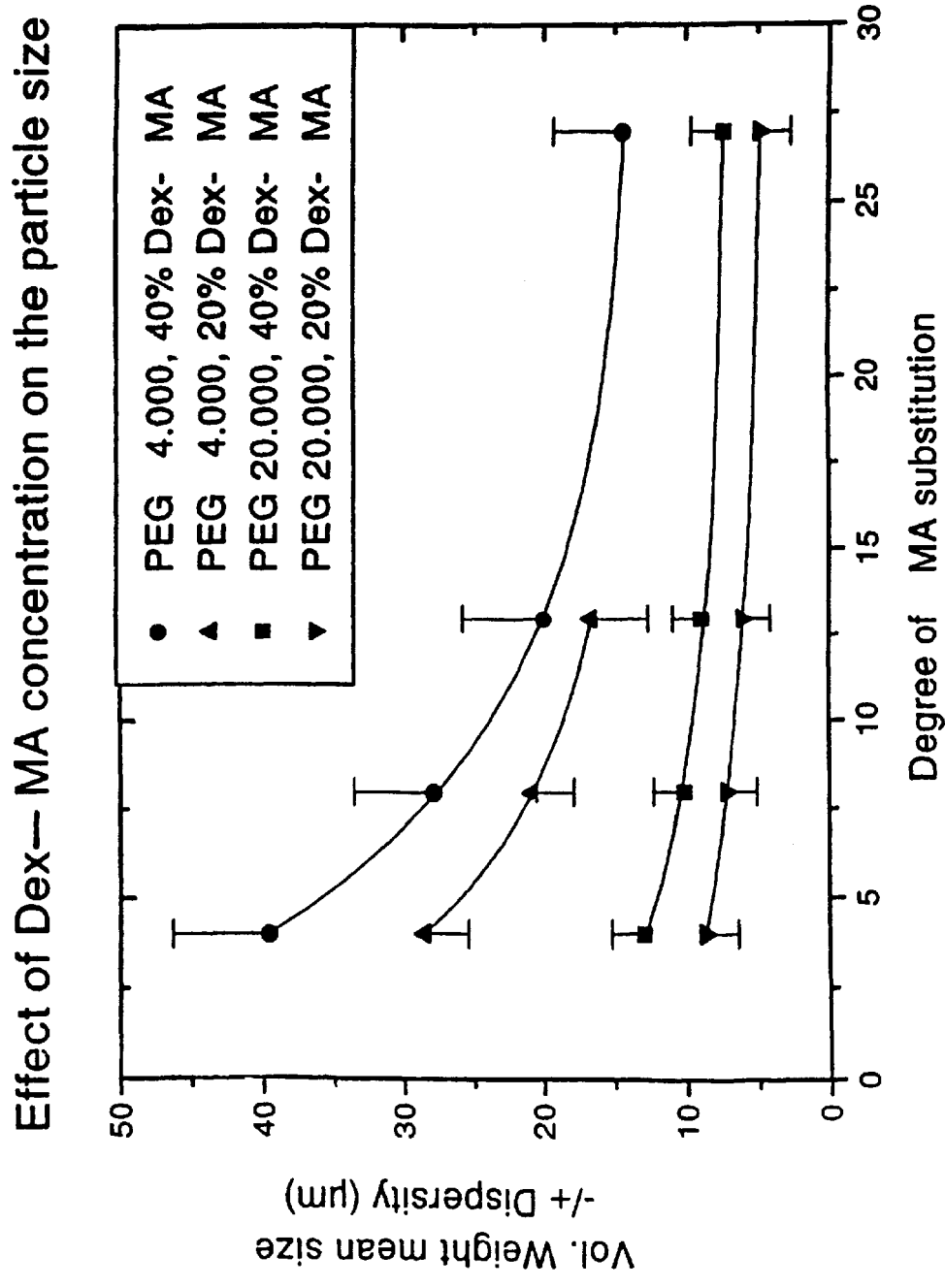
FIG. 4 shows the volume weight average diameter of dextran microspheres as a function of the degree of MA substitution and concentration of the aqueous dex-MA concentration.

FIG. 4 shows the volume weight average diameter of dextran microspheres as a function of the degree of MA substitution and concentration of the aqueous dex-MA concentration. The mean diameter decreases with decreasing dex-MA concentration.

Figure 5:
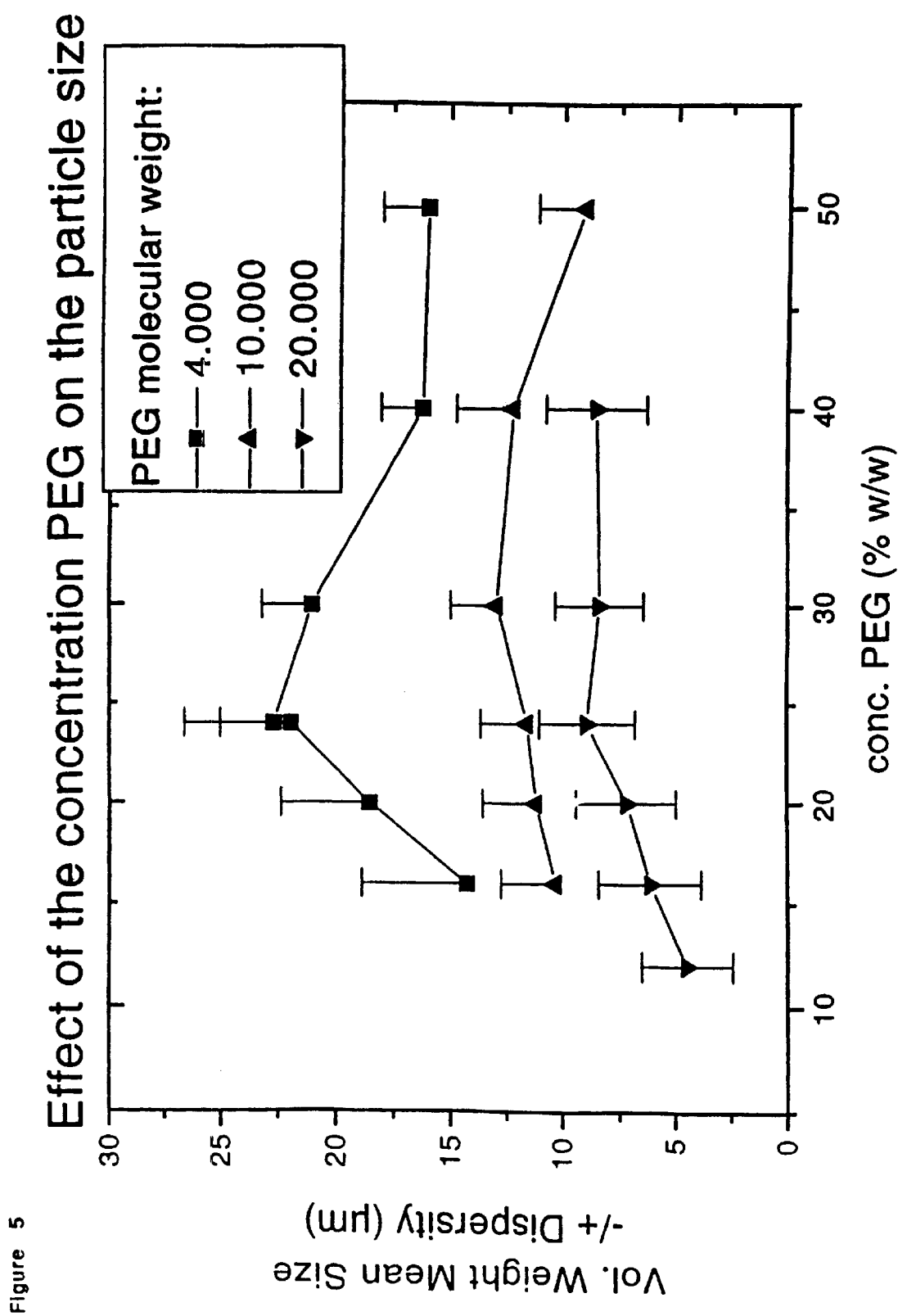
FIG. 5 shows the effect of the concentration and molecular weight of PEG on the volume weight average diameter of dextran microspheres.

FIG. 5 shows the effect of the concentration and molecular weight of PEG on the volume weight average diameter of the dextran microspheres. For this evaluation, dex-MA with a DS of 8 in 0.22 M KCl (20%, w/w) was used. It appears that for a given PEG, the largest particles were obtained at a PEG concentration around 24%.

Example 2

Microspheres were prepared from the following formulations using the protocol as given in Example 1 and using the following stock solutions:

Stock solutions (% in w/w) in 0.22 M KCl:
A. PEG 10.000, 24%
B. PEG 20.000, 24%
C. Dex-MA (DS 13) 20%
D. Dex-lactHEMA (DS 3) 20%
E. Dex-lactHEMA (DS 3) 10%
F. Dex-PEG 20%

TABLE 1

| | summarizes the results: | | | |
|---|---|---|---|---|
| PEG | dex | emulsifier | number weight diameter (μm) | volume weight diameter (μm) |
| 4.50 ml A | 0.25 ml C | 0.25 ml F | 3.3 | 7.2 |
| 4.75 ml A | 0.25 ml C | no | 4.4 | 11.5 |
| 4.75 ml B | 0.25 ml D | no | 6.3 | 17.0 |
| 4.75 ml B | 0.25 ml E | no | 5.3 | 16.0 |

As can be seen, a suitable emulsifier (block-copolymer of dextran and PEG) gives smaller particles with a smaller dispersity (=weight mean diameter/number mean diameter).

Example 3

The release of a model protein from non-degrading dextran microspheres and degradable microspheres was evaluated. The microspheres were rendered degradable by the incorporation of dextranase in dex-MA microspheres.

Dex-MA (DS 8) was dissolved in 10 mM phosphate buffer pH 8.0. To 2 ml of this solution a fixed amount of IgG (Immunoglobuline G, 25.6 mg) and a variable amount of dextranase (Sigma D1508; 0, 0.1 and 1 U (1 U releases 1 μmol reducing oligosaccharides per minute at 37° C. and pH 6.0)) dextranase were added. This solution was emulsified in an aqueous solution of PEG (M 10.000, concentration 24% (w/w)) in 0.22 M KCl. Thereafter, TEMED (N,N,N',N'-tetramethyl-ethylenediamine, 100 μl, 20% (v/v) in 0.22 M KCl, pH adjusted with concentrated HCl to 7.2) and KPS (potassium peroxydisulfate, 180 μl, 50 mg/ml in water) were added. The microspheres were washed with water and dried under a nitrogen flow.

Figure 6:
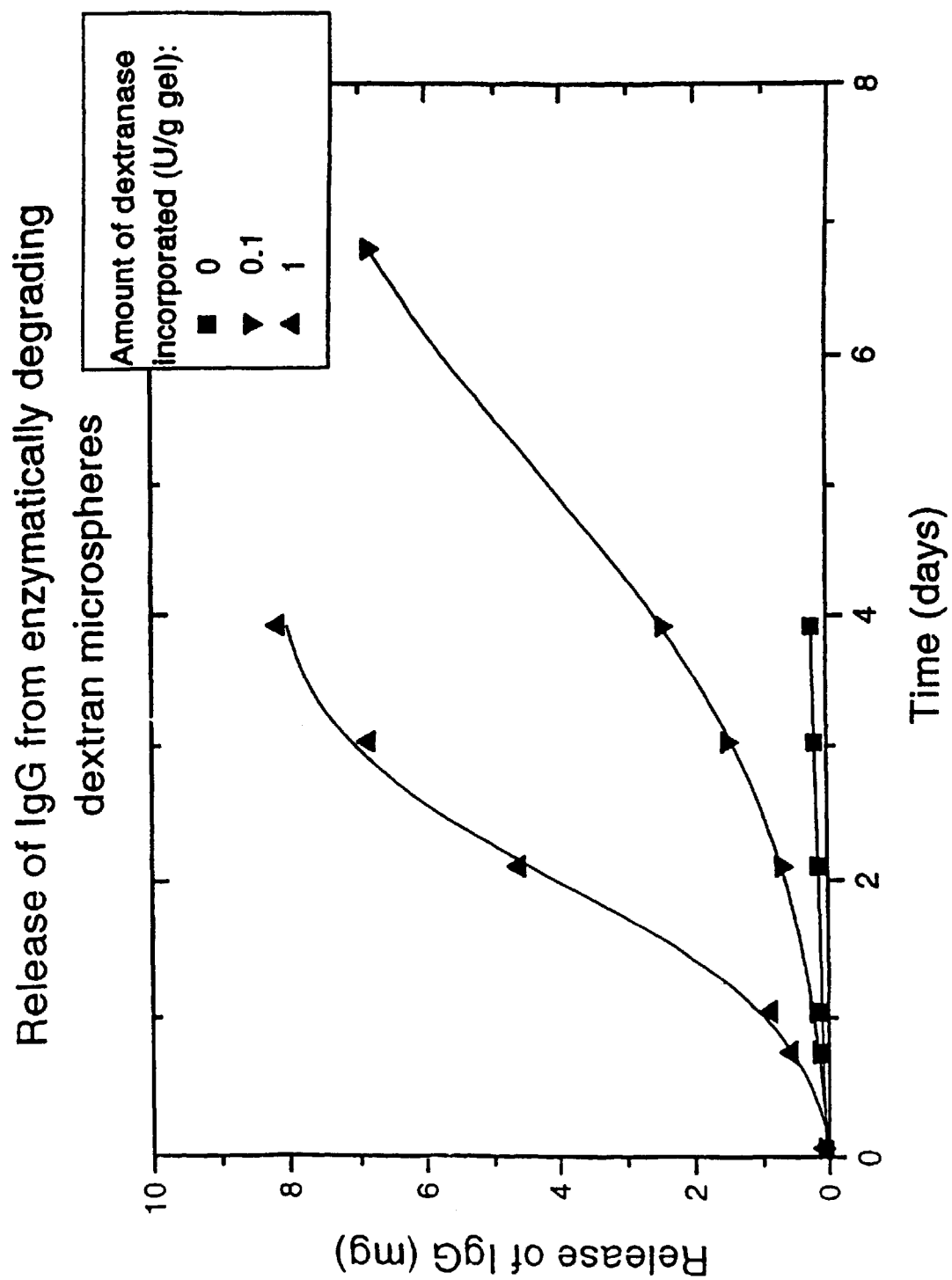
FIG. 6 shows release profiles of degrading dextran microspheres.

An accurately weighed amount (0.3–0.5 g) of microspheres was suspended in 10 ml phosphate buffer pH 5.5 and the amount of protein released in the buffer was determined using the biorad protein assay (M. Bradford. Anal. Biochem. 72 (1976) 248–254). FIG. 6 shows the release profiles. From this figure it is clear that the release of IgG from dextran microspheres can be modulated by dextranase.

Example 4

Reference Example

The release of a model protein (IgG) from degrading dextran microspheres was evaluated. Degradation was established by co-entrapment of dextranase in the microparticles.

Figure 7:
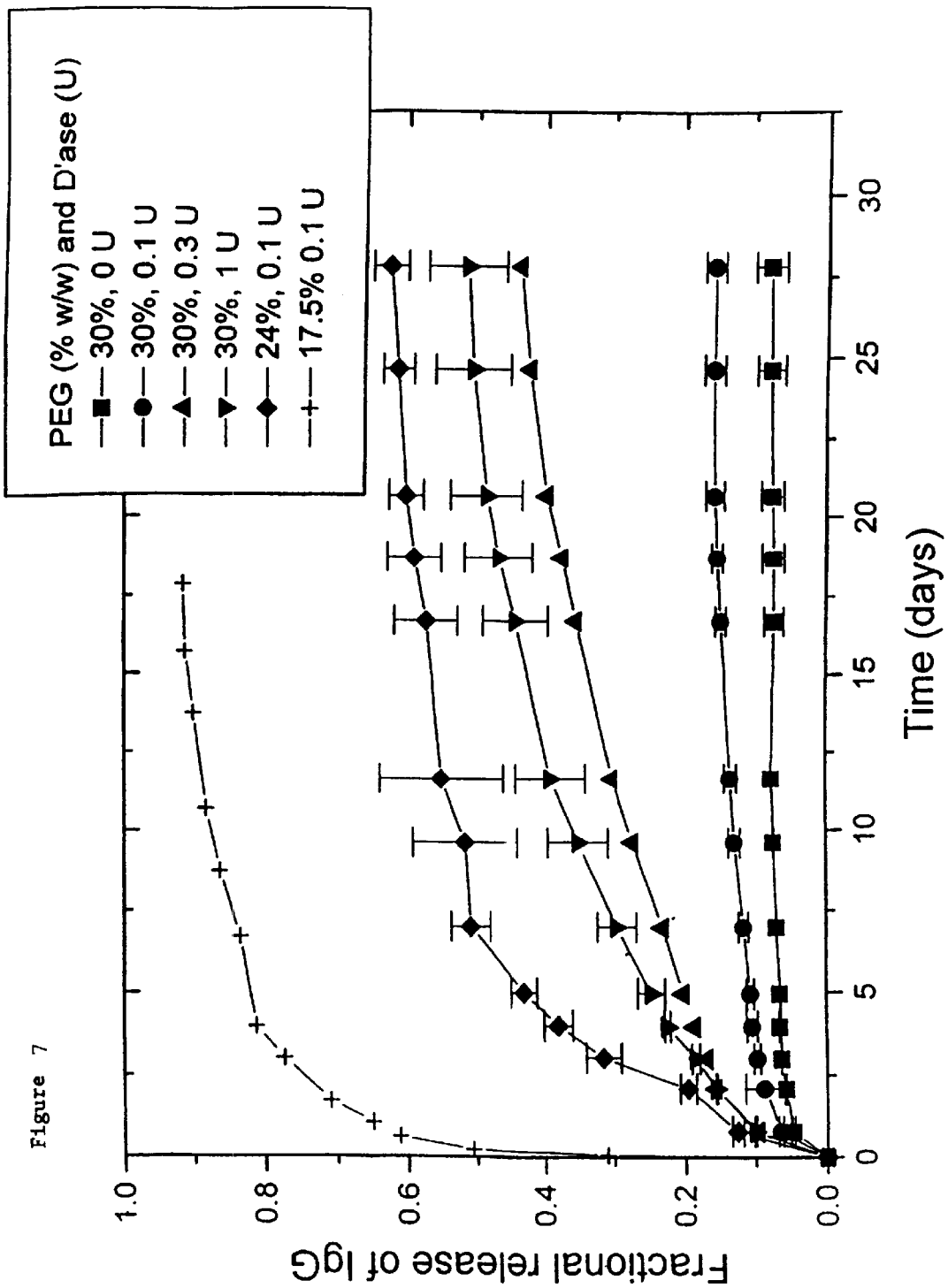
FIG. 7 also shows release profiles of degrading dextran microspheres.
Figure 8:
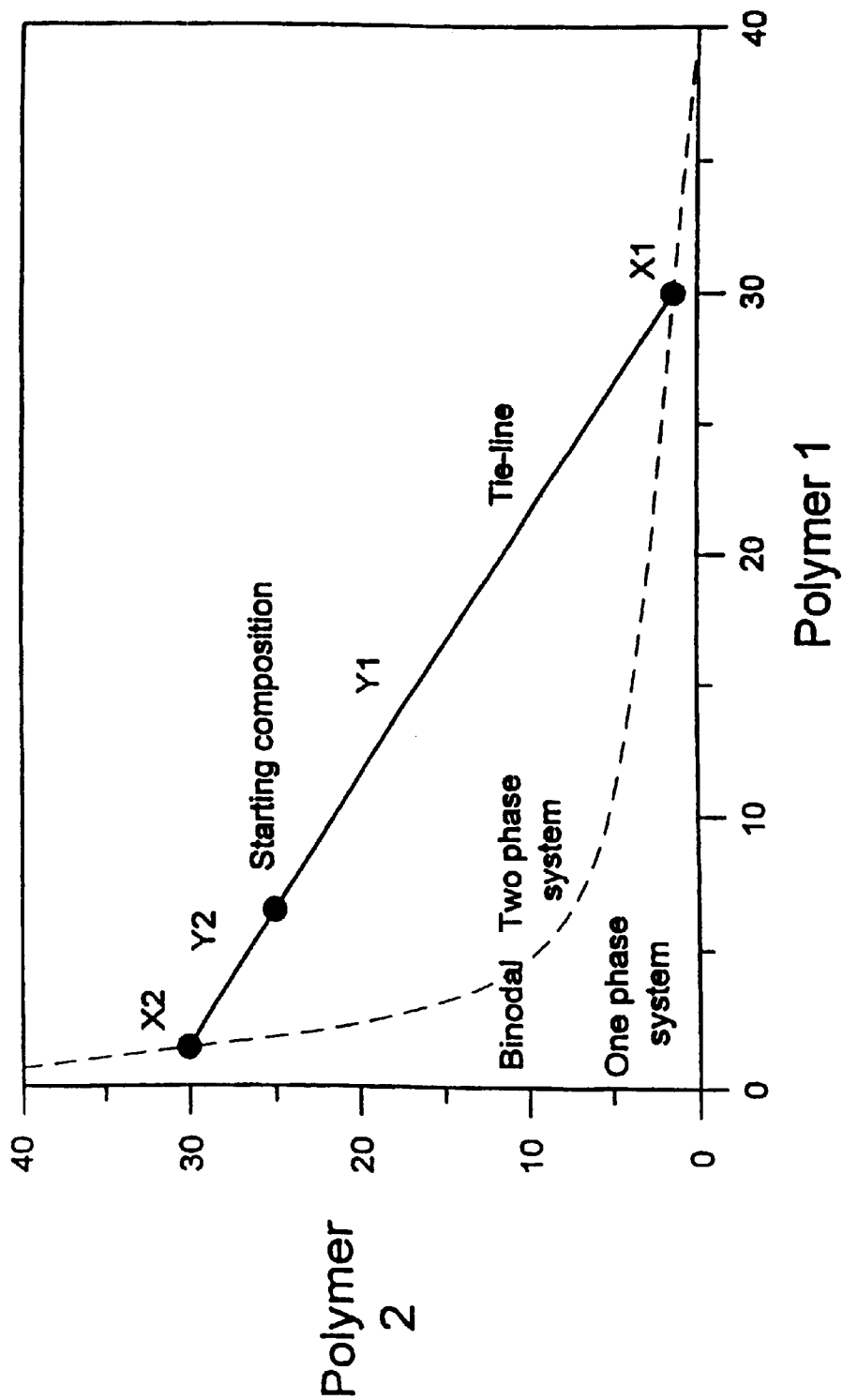
FIG. 8 shows a phase diagram of a water/PEG/dextran ternary system.

Methacrylate derivatized dextran (DS=8; 138 mg) was dissolved in 612 μl buffer (10 mM phosphate, 220 mM KCl, pH 8.0). Thereafter, 250 μl of an aqueous solution of IgG (50 mg/ml) and 250 μl of an aqueous solution of dextranase (variable concentration) were added. IgG and Dextranase were dissolved in the same buffer (10 mM phosphate, 220 mM KCl, pH 8.0). Next, 500 μl of the dexMA, IgG, Dextranase solution was added to 5 ml of an aqueous solution of PEG (molecular weight 10.000 g/mol, concentration 17.5, 24 or 30% w/w) in the same buffer. These phase separated systems were vortexed for 1 minute, followed by the addition of 180 μl potassium peroxodisulphate (50 mg/ml; dissolved in phosphate buffer) and TEMED (N,N, N',N"-tetramethylethylenediamine, 20% v/v, pH adjusted to 8.0 with HCl). Next, the samples were incubated for 30 minutes at 37° C. to polymerize the DexMA. The particles were collected by centrifugation and washed with water. The particles were resuspended in buffer (5 mM NH$_4$Ac, pH 5.5) and incubated at 37° C. Periodically, samples were withdrawn and analyzed for their protein content (Biorad assay). FIG. 7 shows the release profiles. It can be seen that in the absence of dextranase the cumulative release was less than 10%, indicating that the hydrodynamic diameter of protein was larger than the hydrogel mesh size. Further, the release rate increases with increasing amount of dextranase in the particles. An increasing amount of dextranase in the particles resulted in an increasing degradation rate. This means that the release of entrapped proteins form dextran particles can be modulated by the degradation rate of the hydrogel matrix. Degradation can be established by addition of an enzyme (dextranase) or by the introduction of hydrolytically labile spacers (e.g. lactate esters) in the crosslinks.

Comparative Example 5 grams of dextran in which the dextran chains are derivatized with methacrylate groups, having a Mw of 40,000, was dissolved in 45 ml of water. A second solution was prepared, which solution comprised 7 g of polyethylene glycol having a Mw of 6,000 in 45 ml water.

At room temperature, the first solution was added to the second solution while stirring. The result was a one phase system, from which no microspheres could be formed. This example illustrates the need to choose the molecular weights and concentrations of the starting materials in such a way that a two-phase system is obtained.

In the following Examples 5–9 the following materials were used.
Polymer-related Materials PEG 10.000 (M$_w$ 12.000; M$_n$ 8700) and potassium peroxodisulfate were obtained from Merck (Darmstadt, Germany). Dex 40.000 (M$_w$ 38800; M$_n$ 16400) and N,N,N', N'-tetramethylethylenediamine were purchased from Fluka (Buchs, Switzerland). M$_w$ and M$_n$ refer to the weight and the number average molecular weight, respectively (determined by GPC). Methacrylate (MA) derivatized dextran (dexMA) with a degree of substitution (DS: the number of MA groups per 100 dextran glucopyranosyl monomer units) of 10 was prepared as described by Van Dijk-Wolthuis et al. in Macromolecules 28 (1995), 6317–6322. Hydroxyethyl methacrylate (HEMA) derivatized dextran (dexHEMA) with different DS were prepared as described by Van Dijk-Wolthuis et al. The degrees of substitution as determined by $^1$H-HMR were 5, 8 and 16. Monodisperse and polydisperse lactate HEMA derivatized dextran (dexLactateHEMA) were prepared according to Cadée et al. (Polymer 40 (1999) 6877–6881) and Van Dijk-Wolthuis et al. and both had a DS of 4.
Liposome-related Materials Dipalmitoylphosphatidylcholine (DPPC) and dipalmitoylphosphatidylglycerol (DPPG) were donated by Lipoid GmbH (Ludwigshafen, Germany). Cholesterol (Chol) and calcein were obtained from Sigma (Rockford, Ill., USA). Chloroform and methanol (p.a.) were purchased from Merck (Darmstadt, Germany).

Example 5

DPPC:DPPG:Chol (10:1:10) liposomes were prepared by lipid film hydration as described in Crommelin et al. ('Liposomes', In: Kreuter, J. (ed.), Colloidal Drug Delivery Systems. Inc. Marcel Dekker (1994), pp. 73–190), with and without calcein, an aqueous marker used at a concentration of 80 mM as the active ingredient. The incorporation of calcein is described in Gregoriadis (ed.), 'Liposome Technology', Vol. I, II and III, 1st and 2nd edition, CRC Press, Boca Raton, Fla. (1984, 1993).

10 mM Hepes (N-[2-hydroxyethyl]piperazine-N'-[4-butane sultonic acid]) buffer containing 0.8% NaCl, adjusted to pH 7.2 was used as aqueous medium (total lipid concentration 81 mM). Subsequently the liposomes were extruded through 0.6, 0.2, 0.1 and/or 0.05 μm polycarbonate filters to obtain the desired size. The calcein containing liposomes were washed by ultracentrifugation to remove the unentrapped calcein. The phospholipid content was measured by the phosphate determination according to Rousser et al. ('Two-dimensional thin layer chromatographic separation of polar lipids and determination of phospholipids by phosphorous analysis of spots', Lipids 5 (1970) 494–496). Mean particle size was determined by dynamic light scattering (DLS). The size, polydispersity index and phosphate or calcein content of the liposomes prepared are presented in Table 2.

TABLE 2

Liposome size, polydispersity index, phosphate content and calcein content of liposomes used.

| Liposome type | Size (nm) | PD | Phosphate content (mM) | Calcein content (mM) |
|---|---|---|---|---|
| DPPC:DPPG:Chol(10:1:10) | 370 | 0.31 | 36.4 | x |
| | 184 | 0.10 | 35.1 | x |
| | 95 | 0.05 | 27.3 | x |
| DPPC:DPPG:Chol(10:1:10) | 783 | 0.62 | nd | 36 |
| | 226 | 0.18 | nd | 39 |
| | 148 | 0.11 | nd | 29 | nd = not determined

Example 6

Microencapsulated liposomes were prepared by mixing liposomes prepared in Example 5 with an aqueous solution of dexMA in 10 mM Hepes buffer. Two batches were produced, one with calcein present in the liposomes, and one without. Also an aqueous solution of PEG in 10 mM Hepes buffer was prepared. Both solutions were flushed with nitrogen for 10 min before liposomes were added and were subsequently transferred to a scintillation vial (total weight 5 g). The resulting two phase system was vigorously vortexed for 60 s to create a water-in-water emulsion. Next, the emulsion was allowed to stabilize for 10–15 minutes (ambient conditions), followed by the addition of TEMED (100 μl, 20% v/v, adjusted at pH 7 with 4 M HCl) and KPS (180 μl, 50 mg/ml). This system was incubated from 30 min at 37° C. to polymerize the methacrylate groups coupled to the dextran chains. Subsequently, the PEG phase was removed by multiple washing and centrifugation steps. The particle size and size distribution were measured with a laser light blocking technique (Accusizer™).

Different batches were prepared using varying liposome sizes (95, 184 and 370 nm), microsphere water content (50–70%) and PEG/dex volume ratios (20–80).

The encapsulation efficiency of liposomes in the microspheres was defined as the amount of liposomes in the microspheres divided by the amount of liposomes added to the two phase system. The amount of liposomes in the microspheres was determined by measuring the phospholipid concentration in the microsphere pellet using the phosphate determination according to Rousser et al. (Lipids 5 (1970) 494–496).

The encapsulation efficiency was very reproducible. For 5 independently prepared samples (formulation:dexMA DS 10, water content: 70%, volume ratio: 40, liposome size: 184 nm), the encapsulation efficiency was 94.4%. In this case the liposomes were mixed with the dextran phase prior to addition to the PEG phase, in accordance with a preferred embodiment of the invention. When liposomes were added to the phase separated system, this resulted in an encapsulation efficiency of 88.1%. So, mixing the liposomes with the dextran phase first resulted in a higher encapsulation efficiency.

The effects of liposome size, microsphere water content and PEG/dex volume ratio on the encapsulation efficiency were studied and are presented in Table 3.

TABLE 3

Effect of water content, PEG/dextran volume ratio and liposome size on encapsulation efficiency (using DPPC:DPPG:Chol (10:1:10) liposomes and dexMA DS 10).

| Water content (%) | Volume ratio | Liposome size (nm) | Encapsulation efficiency (%) |
|---|---|---|---|
| 70 | 20 | 370 | 90 |
| 70 | 20 | 184 | 88 |
| 70 | 20 | 95 | 89 |
| 70 | 40 | 370 | 97 |
| 70 | 40 | 184 | 92 |
| 70 | 40 | 95 | 102 |
| 70 | 80 | 370 | 56 |
| 70 | 80 | 184 | 83 |
| 70 | 80 | 95 | 91 |
| 50 | 20 | 370 | 102 |
| 50 | 20 | 184 | 99 |
| 50 | 20 | 95 | 96 |
| 50 | 40 | 370 | 104 |
| 50 | 40 | 184 | 100 |
| 50 | 40 | 95 | 103 |
| 50 | 80 | 370 | 76 |
| 50 | 80 | 184 | 88 |
| 50 | 80 | 95 | 90 |

From this table 3 it appears that in most cases, the encapsulation efficiency is close to 100%. There seems no relation between the liposome size and the encapsulation efficiency (for any water content and/or volume ratio). The encapsulation efficiency was expected to increase when larger liposomes were used, but apparently even the smallest liposomes were completely entrapped in the dextran matrix. A higher encapsulation efficiency was expected to a lower water content, because a lower water content results in smaller pores in the hydrogel. However, Table 3 shows that there is no relation between the water content and the encapsulation efficiency. For a volume ratio of 80, the encapsulation efficiency is slightly lower, because a large PEG/dex volume ratio results in a small volume of the dextran phase and therefore the liposomes can be less well encapsulated.

Example 7

Example 6 was repeated using dexHEMA instead of dexMA as the crosslinkable polymer. All other steps were the same.

Example 8

Example 6 was repeated using dexLactateHEMA instead of dexMA as the crosslinkable polymer. All other steps were the same.

Example 9

The release of liposomes from the microspheres was measured by incubating the resuspended microspheres (in 10 ml Hepes buffer of desired pH) at 37° C. At desired time points and after centrifugation (10 min, 4500 rpm), the complete supernatant was removed. The microsphere pellet was resuspended in 10 ml fresh buffer and put back at the roller bench. The amount of liposomes in the supernatant was determined by the phosphate determination according to Rousser et al. (Lipids 5 (1970) 494–496). The integrity of the released liposomes was studied using calcein containing liposomes and determining the fluorescence ($\lambda_{ex}$=485, $\lambda_{em}$= 512 nm) of both the untreated supernatant and the supernatant treated with triton X-100. Due to the high concentration of calcein inside the liposomes, quenching occurs, resulting in a low fluorescent signal for intact liposomes. If calcein is released in the surrounding medium, the calcein is diluted resulting in a higher fluorescent signal. Treatment with triton X-100 results in destruction of the liposomes and the release of all calcein. The difference between the release of free calcein and the release of total calcein (after treatment with triton X-100) was used to determine the amount of intact liposomes released.

Most formulations showed pulsed release behavior. The release curve of a sample prepared in Example 2 is presented in FIG. 9 This Figure shows that the release of liposomes from dextran microspheres is very reproducible (n=3). The shape of the curve suggests bulk degradation of the microspheres. Initially only about 10% of the liposomes was released, probably due to release of liposomes present at the surface of the microspheres. Hydrolysis of the microspheres results in increasing pore-size and after a lag-time of about 18 days the rest of the liposomes were set free, giving 100% recovery.

To test whether the liposomes were released intact, the release of calcein containing liposomes was studied. In FIG. 10, the release curves for free calcein, total calcein, liposomal calcein and phosphate are presented for a sample of Example 2. It is obvious that hardly any free calcein is released. However, after treatment of the samples with triton X-100, high fluorescence was measured, indicating that the calcein was still inside the liposomes. Furthermore, the release curves determined by phosphate determination and calcein fluorescence are quite similar. This indicates that the liposomes are released from the microspheres intact. This was also confirmed by dynamic light scattering (DLS) measurements of the released liposomes, the results of which are given in Table 4.

TABLE 4

Liposome size and polydispersity index (PD) before encapsulation and after release from the microspheres.

| Before encapsulation | | After release | |
|---|---|---|---|
| Size (nm) | PD | Size (nm) | PD |
| 370 | 0.31 | 342 | 0.35 |
| 184 | 0.10 | 196 | 0.14 |
| 95 | 0.05 | 102 | 0.19 |

From Table 4, it is clear that the particle size after release is similar to the particle size before encapsulation in the microspheres. The effect of the liposome size on the release characteristics is presented in FIGS. 11A and 11B for pH 7.2 and 8.0, respectively. From both figures it is clear that the liposome size does not affect the delay time. Furthermore, from FIGS. 11A and 11B it follows that the pulse length varies only little with particle size.

In FIG. 12, the effect of the PEG/dextran volume ratio on the release characteristics is presented. As expected, lower volume ratio results in a longer pulse, because a lower volume ratio results in a larger volume of the dextran phase. Therefore, more cross-links have to be degraded to release all liposomes, resulting in a longer pulse. The onset of the pulse was not affected by the volume ratio, because the pore size and the degradation rate is the same, irrespective of the volume of the dextran phase.

The effect of water content on release is given in FIG. 13A. Release over a longer period was observed. However, the lag-time did not increase for lower water contents, although the amount of initially released liposomes was smaller for the microspheres with the lower water contents. The above-mentioned effects of the water content were not observed when dexHEMA with a lower degree of substitution was used (FIG. 13B). This can be explained by the fact that hydrogels with DS smaller than 10 are not dimensionally stable and therefore swell.

Other effects of the degree of substitution on the release characteristics are presented in FIGS. 14A and 14B. From FIG. 14A, it is clear that formulations with a higher DS release the liposomes after a longer delay-time and that the slope of the pulse is less steep. Therefore, the total release time is longer. The smaller slope of the pulse was also observed at pH 8.0 (FIG. 14B). When DS 16 was used, an almost zero-order release was obtained, whereas using DS 5 resulted in a sharp pulse. At this pH, however, the differences in delay-time (as soon for pH 7.2) were not observed.

Besides dexHEMA, the release of liposomes from dex-LactateHEMA microspheres (both monodisperse and polydisperse) was studied as well. In FIG. 15, the release profiles of dexHEMA (DS 5) and dexLactateHEMA (DS 4) microspheres are compared. The release from dexLactate-HEMA microspheres was much faster, because the lactate ester present in dexLactateHEMA is more susceptible to hydrolysis than the carbonate ester present in dexHEMA. There was no difference observed between mono- and polydisperse dexLactateHEMA, because the degrading lactate ester is the same in both polymers. Advantages of monodisperse dexLactateHEMA, however, are that it dissolves more readily and that it results in a more well-defined network.

The release was studied at both pH 7.2 and pH 8.0. Because at these pH values, the degradation of the hydrogel is fully basic catalyzed, the release rate theoretically is linear proportional to the concentration $OH^-$. The pH of the release buffers were set at 7.2 and 8.0 (room-temperature), but at 37° C. (release-temperature) they were 7.1 and 7.8, respectively. Therefore, the concentration $OH^-$ is 4.9 times higher for pH 7.8 than for pH 7.1, so the release was expected to be 4.9 times faster for the highest pH. In Table 5, the ratio between the time where 50% of the liposomes are released for both pH values are represented.

TABLE 5

The theoretically expected and experimentally found effects of the pH on the release rate of the liposomes from dexHEMA microspheres.

| Water content (%) | Degree of substitution | PEG/dex Vol. ratio | Liposome size (nm) | [OH-] ratio | 50% rel. ratio |
|---|---|---|---|---|---|
| 70 | 8 | 40 | 370 | 4.9 | 4.2 |
| 70 | 8 | 40 | 184 | 4.9 | 4.2 |
| 70 | 8 | 40 | 95 | 4.9 | 4.2 |
| 70 | 8 | 20 | 184 | 4.9 | 5.3 |
| 70 | 8 | 80 | 184 | 4.9 | 4.1 |
| 50 | 8 | 40 | 184 | 4.9 | 5.3 |
| 70 | 5 | 40 | 184 | 4.9 | 2.5 |
| 50 | 5 | 40 | 184 | 4.9 | 2.5 |

The theoretically expected difference in release rate correspond well with the values found experimentally. The discrepancy observed from DS=5 again can be explained by swelling of the hydrogel.

What is claimed is:

1. A method for preparing microspheres encapsulating colloidal systems, which method comprises the steps of:
 a) providing an aqueous mixture of
  i) a first phase comprising a first water soluble crosslinkable polymer,
  ii) a second phase comprising a second water soluble polymer which is incompatible in solution with the polymer in said first phase, and
  iii) colloidal systems to be suspended in said first phase;
 b) forming an emulsion of said first phase in said second phase;
 c) forming microspheres in the emulsion by crosslinking at least part of said crosslinkable polymer, thus forming said microspheres encapsulating colloidal systems; and
 d) recovering the microspheres;
 wherein said colloidal systems are selected from the group consisting of liposomes, iscoms, polyplexes, lipoplexes, nanoparticles, solid lipid particles in the colloidal size range, emulsions, and combinations thereof.

2. The method of claim 1, in which step a) is carried out by forming a premixture by contacting said colloidal systems with said first phase, and subsequently contacting this premixture with said second phase.

3. The method of claim 1, in which said crosslinkable polymer is a dextran polymer which comprises crosslinkable groups.

4. The method of claim 3, in which said crosslinkable groups are methacrylate groups.

5. The method of claim 4, in which said dextran polymer is selected from the group consisting of dexMA, dexHEMA and dexLactateHEMA.

6. The method of claim 5, in which the degree of substitution of said dextran polymer is from 2 to 30.

7. The method of claim 1, in which said polymer in the second phase is selected from the group consisting of polyethylene glycol (PEG) and polyvinyl alcohol (PVA).

8. The method of claim 1, wherein said colloidal systems comprise an active ingredient.

9. Microspheres, at least 80 wt. % thereof having a particle diameter of between 100 nm and 100 μm, which microspheres are comprised of a degradable crosslinked polymer which encapsulates colloidal systems wherein said colloidal systems are selected from the group consisting of liposomes, iscoms, polyplexes, lipoplexes, nanoparticles, solid lipid particles in the colloidal size range, emulsions, and combinations thereof.

10. Microspheres according to claim 9, being free from organic solvent.

11. Microspheres according to claim 9, wherein said colloidal systems comprise an active ingredient.

12. The method of claim 8, wherein said active ingredient is a protein drug.

13. The microspheres of claim 9, wherein at least 80% of said microspheres have a particle diameter of between 5 and 15 μm.

14. The microspheres of claim 11, wherein said active ingredient is a protein drug.

15. Microspheres prepared by the method of claim 1.

16. The method of claim 1, wherein said microspheres effect a pulsed release profile of the colloidal systems with a desired lag time.

17. The method of claim 1, wherein said emulsion is a ternary two phase system of
 (1) said first water-soluble polymer which is crosslinkable;
 (2) said second water-soluble polymer, and
 (3) water,
 wherein said ternary system is characterized by a phase diagram and wherein said ternary system forms one phase when composition of the ternary system is below the binodal in said phase diagram and forms two phases when the composition of the ternary system is above the binodal in said phase diagram, and wherein the composition of said ternary two phase system provided is above said binodal and is capable of forming a continuous phase and a discontinuous phase;
 and wherein said emulsion comprises a continuous and discontinuous phase, wherein said first, crosslinkable, polymer is the discontinuous phase in said two-phase system and the second polymer is the continuous phase in said two-phase system, said two phase system having been obtained by adjusting the amounts of water, first polymer and second polymer so as to place the system above the binodal, and
 wherein said colloidal system is present in said two-phase system.

18. The method of claim 1, wherein the degree of crosslinking and water content are adjusted so as to result in pore sizes in said microspheres which are equal to or less than the hydrodynamic diameter of the colloidal system, said pores thus entrapping said colloidal system.

19. The method of claim 1, wherein said first crosslinkable polymer, when crosslinked, can be degraded by virtue of comprising bonds that are hydrolyzable under physiological conditions, and said degradation of the crosslinked polymer occurs through hydrolyzing said bonds.

20. The method of claim 1, wherein said first crosslinkable polymer, when crosslinked, can be degraded by virtue of including, in said microspheres, at least one enzyme which degrades said polymer, and wherein said degradation of crosslinked polymer occurs through action of said enzyme on said polymer.

21. The method of claim 20, wherein said first crosslinkable polymer is dextran or derivatized dextran and the enzyme which degrades the polymer is dextranase.

22. The method of claim 1, wherein said crosslinking is formed by crosslinking methacrylate or a methacrylate derivative or by using isocyanate or through poly-N-isopropyl acrylamide.

23. The method of claim 1, wherein step (d) is performed by filtration or centrifugation.

24. The microspheres of claim 9, wherein said microspheres effect a pulsed release profile of the colloidal system with a desired lag time.

25. The microspheres of claim 9, wherein the pore size of the crosslinked polymer is equal to or less than the hydrodynamic diameter of the colloidal system.

26. The microspheres of claim 9, wherein said degradable, crosslinked polymer is selected from the group consisting of dextran, derivatized dextran, starch, starch derivatives, cellulose derivatives, proteins and derivatized proteins.

27. The microspheres of claim 26, wherein said degradable, crosslinked polymer is dextran or a derivatized dextran.

28. The microspheres of claim 27, wherein said derivatized dextran comprises methacrylate groups.

29. The microspheres of claim 28, wherein said derivatized dextran is dexMA, dexHEMA or dexLactateHEMA.

* * * * *

UNITED STATES PATENT AND TRADEMARK OFFICE
CERTIFICATE OF CORRECTION

PATENT NO. : 6,395,302 B1
DATED : May 28, 2002
INVENTOR(S) : Wilhelmus Everhardus Hennink and Okke Franssen It is certified that error appears in the above-identified patent and that said Letters Patent is hereby corrected as shown below:

<u>Title page,</u>
Item [73], Assignee, delete "Octoplus B.V. (NL)" and insert -- OctoPlus B.V. (NL) --.

Signed and Sealed this

Nineteenth Day of November, 2002

Attest:

Attesting Officer

JAMES E. ROGAN
Director of the United States Patent and Trademark Office